United States Patent
Voss

(10) Patent No.: US 9,173,644 B2
(45) Date of Patent: Nov. 3, 2015

(54) CLOSURE DEVICES, SYSTEMS, AND METHODS

(75) Inventor: Laveille K. Voss, Belmont, CA (US)

(73) Assignee: ABBOTT VASCULAR INC., Santa Clara, CA (US)

(*) Notice: Subject to any disclaimer, the term of this patent is extended or adjusted under 35 U.S.C. 154(b) by 155 days.

(21) Appl. No.: 12/684,400

(22) Filed: Jan. 8, 2010

(65) Prior Publication Data

US 2010/0179571 A1    Jul. 15, 2010

Related U.S. Application Data

(60) Provisional application No. 61/143,751, filed on Jan. 9, 2009.

(51) Int. Cl.
| | |
|---|---|
| *A61B 17/08* | (2006.01) |
| *A61B 17/00* | (2006.01) |
| *A61B 17/064* | (2006.01) |
| *A61B 17/068* | (2006.01) |

(52) U.S. Cl.
CPC ........... *A61B 17/0057* (2013.01); *A61B 17/068* (2013.01); *A61B 17/0644* (2013.01); *A61B 2017/00659* (2013.01); *A61B 2017/00668* (2013.01); *A61B 2017/00672* (2013.01); *A61B 2017/00867* (2013.01); *A61B 2017/0645* (2013.01)

(58) Field of Classification Search
CPC ........... A61B 17/0057; A61B 17/0644; A61B 2017/00659; A61B 2017/00668; A61B 2017/00672; A61B 2017/0645; A61B 2017/00575; A61M 25/04; A61M 2025/0293; A61J 15/0038

USPC ......... 606/142, 151, 157, 158, 213, 215, 216, 606/219–221

See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 556,082 A | 3/1896 | Boeddinghaus |
| 1,088,393 A | 2/1914 | Backus |
| 1,123,290 A | 1/1915 | Von Herff |
| 1,242,139 A | 10/1917 | Callahan |
| 1,331,401 A | 2/1920 | Summers |
| 1,480,935 A | 1/1924 | Gleason |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

U.S. Appl. No. 12/114,031, May 11, 2011, Office Action.

(Continued)

*Primary Examiner* — Alexander Orkin
(74) *Attorney, Agent, or Firm* — Workman Nydegger; Randy Shen

(57) ABSTRACT

The present disclosure includes vessel closure devices, systems, and methods. A closure system configured to close a body lumen opening may include a handle member. A tube set configured to deliver and/or deploy a closure element may be coupled to the handle member. The closure system may also include an inner lumen with an anchor member at least partially disposed in the inner lumen. A plunger member may be movably coupled to the handle member.

24 Claims, 20 Drawing Sheets

(56) References Cited

U.S. PATENT DOCUMENTS

| | | |
|---|---|---|
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vailancourt |
| 4,526,174 A | 7/1985 | Froehlich |
| 4,570,633 A | 2/1986 | Golden |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |

(56) References Cited

U.S. PATENT DOCUMENTS

| | | |
|---|---|---|
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,454,413 A | 10/1995 | Morelli |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Lindon et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |

(56) References Cited

U.S. PATENT DOCUMENTS

| | | | |
|---|---|---|---|
| 5,681,334 A | 10/1997 | Evans et al. | |
| 5,683,405 A | 11/1997 | Yacoubian et al. | |
| 5,690,674 A | 11/1997 | Diaz | |
| 5,695,504 A | 12/1997 | Gifford, III et al. | |
| 5,695,505 A | 12/1997 | Yoon | |
| 5,695,524 A | 12/1997 | Kelley et al. | |
| 5,697,943 A | 12/1997 | Sauer et al. | |
| 5,700,273 A | 12/1997 | Buelna et al. | |
| 5,709,224 A | 1/1998 | Behl et al. | |
| 5,713,899 A | 2/1998 | Marnay et al. | |
| 5,715,987 A | 2/1998 | Kelley et al. | |
| 5,716,375 A | 2/1998 | Fowler | |
| 5,720,755 A | 2/1998 | Dakov | |
| 5,725,498 A | 3/1998 | Janzen et al. | |
| 5,725,552 A | 3/1998 | Kotula et al. | |
| 5,725,554 A | 3/1998 | Simon et al. | |
| 5,728,110 A | 3/1998 | Vidal et al. | |
| 5,728,114 A | 3/1998 | Evans et al. | |
| 5,728,116 A | 3/1998 | Rosenman | |
| 5,728,122 A | 3/1998 | Leschinsky et al. | |
| 5,728,132 A | 3/1998 | Van Tassel et al. | |
| 5,728,133 A | 3/1998 | Kontos | |
| 5,732,872 A | 3/1998 | Bolduc et al. | |
| 5,735,736 A | 4/1998 | Volk | |
| 5,735,873 A | 4/1998 | MacLean | |
| 5,749,826 A | 5/1998 | Faulkner | |
| 5,752,966 A | 5/1998 | Chang | |
| 5,755,726 A | 5/1998 | Pratt et al. | |
| 5,755,727 A * | 5/1998 | Kontos | 606/144 |
| 5,755,778 A | 5/1998 | Kleshinski | |
| 5,766,217 A | 6/1998 | Christy | |
| 5,766,246 A | 6/1998 | Mulhauser et al. | |
| 5,769,870 A | 6/1998 | Salahieh et al. | |
| 5,776,147 A | 7/1998 | Dolendo | |
| 5,779,707 A | 7/1998 | Bertholet et al. | |
| 5,780,807 A | 7/1998 | Saunders | |
| 5,782,844 A | 7/1998 | Yoon et al. | |
| 5,782,860 A | 7/1998 | Epstein et al. | |
| 5,782,861 A | 7/1998 | Cragg et al. | |
| 5,795,958 A | 8/1998 | Rao et al. | |
| 5,797,928 A | 8/1998 | Kogasaka | |
| 5,797,931 A | 8/1998 | Bito et al. | |
| 5,797,933 A | 8/1998 | Snow et al. | |
| 5,797,958 A | 8/1998 | Yoon | |
| 5,797,960 A | 8/1998 | Stevens et al. | |
| 5,810,776 A | 9/1998 | Bacich et al. | |
| 5,810,846 A | 9/1998 | Virnich et al. | |
| 5,810,851 A | 9/1998 | Yoon | |
| 5,817,113 A | 10/1998 | Gifford, III et al. | |
| 5,820,631 A | 10/1998 | Nobles | |
| 5,827,298 A | 10/1998 | Hart et al. | |
| 5,830,125 A | 11/1998 | Scribner et al. | |
| 5,830,217 A | 11/1998 | Ryan | |
| 5,830,221 A | 11/1998 | Stein et al. | |
| 5,833,698 A | 11/1998 | Hinchliffe et al. | |
| 5,843,164 A | 12/1998 | Frantzen et al. | |
| 5,843,167 A | 12/1998 | Dwyer et al. | |
| 5,845,657 A | 12/1998 | Carberry et al. | |
| 5,853,421 A | 12/1998 | Leschinsky et al. | |
| 5,853,422 A | 12/1998 | Huebsch et al. | |
| 5,855,312 A | 1/1999 | Toledano | |
| 5,858,082 A | 1/1999 | Cruz et al. | |
| 5,860,991 A | 1/1999 | Klein et al. | |
| 5,861,003 A | 1/1999 | Latson et al. | |
| 5,861,005 A | 1/1999 | Kontos | |
| 5,868,755 A | 2/1999 | Kanner et al. | |
| 5,868,762 A | 2/1999 | Cragg et al. | |
| 5,868,763 A | 2/1999 | Spence et al. | |
| 5,871,474 A | 2/1999 | Hermann et al. | |
| 5,871,501 A | 2/1999 | Leschinsky et al. | |
| 5,871,525 A | 2/1999 | Edwards et al. | |
| 5,873,876 A | 2/1999 | Christy | |
| 5,873,891 A | 2/1999 | Sohn | |
| 5,879,366 A | 3/1999 | Shaw et al. | |
| 5,891,088 A | 4/1999 | Thompson et al. | |
| 5,897,487 A | 4/1999 | Ouchi | |
| 5,902,310 A | 5/1999 | Foerster et al. | |
| 5,904,697 A | 5/1999 | Gifford, III et al. | |
| 5,904,703 A | 5/1999 | Gilson | |
| 5,906,631 A | 5/1999 | Imran | |
| 5,907,893 A | 6/1999 | Zadno-Azizi et al. | |
| 5,908,149 A | 6/1999 | Welch et al. | |
| 5,910,155 A | 6/1999 | Ratcliff et al. | |
| 5,919,207 A | 7/1999 | Taheri | |
| 5,922,009 A | 7/1999 | Epstein et al. | |
| 5,928,231 A | 7/1999 | Klein et al. | |
| 5,928,251 A | 7/1999 | Aranyi et al. | |
| 5,928,260 A | 7/1999 | Chin et al. | |
| 5,935,147 A | 8/1999 | Kensey et al. | |
| 5,938,667 A | 8/1999 | Peyser et al. | |
| 5,941,890 A | 8/1999 | Voegele et al. | |
| 5,947,999 A | 9/1999 | Groiso | |
| 5,948,001 A | 9/1999 | Larsen | |
| 5,951,518 A | 9/1999 | Licata et al. | |
| 5,951,575 A | 9/1999 | Bolduc et al. | |
| 5,951,576 A | 9/1999 | Wakabayashi | |
| 5,951,589 A | 9/1999 | Epstein et al. | |
| 5,954,732 A | 9/1999 | Hart et al. | |
| 5,957,900 A | 9/1999 | Ouchi | |
| 5,957,936 A | 9/1999 | Yoon et al. | |
| 5,957,938 A | 9/1999 | Zhu et al. | |
| 5,957,940 A | 9/1999 | Tanner et al. | |
| 5,964,782 A | 10/1999 | Lafontaine et al. | |
| 5,972,023 A | 10/1999 | Tanner et al. | |
| 5,976,161 A | 11/1999 | Kirsch et al. | |
| 5,976,174 A | 11/1999 | Ruiz | |
| 5,984,934 A | 11/1999 | Ashby et al. | |
| 5,984,948 A | 11/1999 | Hasson | |
| 5,984,949 A | 11/1999 | Levin | |
| 5,993,468 A | 11/1999 | Rygaard | |
| 5,993,476 A | 11/1999 | Groiso | |
| 6,001,110 A | 12/1999 | Adams | |
| 6,004,341 A | 12/1999 | Zhu et al. | |
| 6,007,563 A | 12/1999 | Nash et al. | |
| 6,010,517 A | 1/2000 | Baccaro | |
| 6,013,084 A | 1/2000 | Ken et al. | |
| 6,015,815 A | 1/2000 | Mollison | |
| 6,019,779 A | 2/2000 | Thorud et al. | |
| 6,022,372 A | 2/2000 | Kontos | |
| 6,024,750 A | 2/2000 | Mastri | |
| 6,024,756 A | 2/2000 | Huebsch et al. | |
| 6,030,364 A | 2/2000 | Durgin et al. | |
| 6,030,413 A | 2/2000 | Lazarus | |
| 6,033,427 A | 3/2000 | Lee | |
| 6,036,703 A | 3/2000 | Evans et al. | |
| 6,036,720 A | 3/2000 | Abrams et al. | |
| 6,045,570 A | 4/2000 | Epstein et al. | |
| 6,048,358 A | 4/2000 | Barak | |
| 6,056,768 A | 5/2000 | Cates et al. | |
| 6,056,769 A | 5/2000 | Epstein et al. | |
| 6,056,770 A | 5/2000 | Epstein et al. | |
| 6,059,800 A | 5/2000 | Hart et al. | |
| 6,059,825 A | 5/2000 | Hobbs et al. | |
| 6,063,085 A | 5/2000 | Tay et al. | |
| 6,063,114 A | 5/2000 | Nash et al. | |
| 6,071,300 A | 6/2000 | Brenneman et al. | |
| 6,074,395 A | 6/2000 | Trott et al. | |
| 6,077,281 A | 6/2000 | Das | |
| 6,077,291 A | 6/2000 | Das | |
| 6,080,182 A | 6/2000 | Shaw et al. | |
| 6,080,183 A | 6/2000 | Tsugita et al. | |
| 6,083,242 A | 7/2000 | Cook | |
| 6,090,130 A | 7/2000 | Nash et al. | |
| 6,095,155 A | 8/2000 | Criscuolo | |
| 6,102,271 A | 8/2000 | Longo et al. | |
| 6,110,184 A | 8/2000 | Weadock | |
| 6,113,610 A | 9/2000 | Poncet | |
| 6,113,612 A | 9/2000 | Swanson et al. | |
| 6,117,125 A | 9/2000 | Rothbarth et al. | |
| 6,117,148 A | 9/2000 | Ravo | |
| 6,117,157 A | 9/2000 | Tekulve | |
| 6,117,159 A | 9/2000 | Huebsch et al. | |
| 6,120,524 A | 9/2000 | Taheri | |
| 6,126,675 A | 10/2000 | Schervinsky et al. | |

(56) References Cited

U.S. PATENT DOCUMENTS

| | | |
|---|---|---|
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,276,704 B1 | 8/2001 | Suiter |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |

(56) References Cited

U.S. PATENT DOCUMENTS

| | | |
|---|---|---|
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Beckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,780,696 B2 | 8/2010 | Daniel et al. |
| 7,799,042 B2 | 9/2010 | Williamson, IV et al. |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelöv |
| 8,226,666 B2 | 7/2012 | Zarbatany et al. |
| 8,409,228 B2 | 4/2013 | Blatter et al. |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2004/0009205 A1 | 1/2004 | Sawhney |
| 2004/0009289 A1 | 1/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |

(56) References Cited

U.S. PATENT DOCUMENTS

| | | |
|---|---|---|
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267524 A1 | 12/2005 | Chanduszko |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0195125 A1 | 8/2006 | Sakakine et al. |
| 2006/0206146 A1 | 9/2006 | Tenerz |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049968 A1* | 3/2007 | Sibbitt et al. ................. 606/213 |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0208225 A1 | 8/2008 | Seibold et al. |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312666 A1 | 12/2008 | Ellingwood et al. |
| 2008/0312667 A1* | 12/2008 | Drasler et al. ................. 606/144 |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |

(56) References Cited

U.S. PATENT DOCUMENTS

| | | | |
|---|---|---|---|
| 2009/0105728 A1 | 4/2009 | Noda et al. |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0171388 A1 | 7/2009 | Dave et al. |
| 2009/0177212 A1 | 7/2009 | Carley et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0066163 A1 | 3/2011 | Cho et al. |
| 2011/0082495 A1 | 4/2011 | Ruiz |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Kariniemi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0142624 A1 | 5/2014 | Pantages et al. |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |

(56) References Cited

FOREIGN PATENT DOCUMENTS

| | | |
|---|---|---|
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 12/143,020, May 11, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/667,144, Oct. 28, 2011, Notice of Allowance.
U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Office Action.
U.S. Appl. No. 12/684,470, Dec. 20, 2011, Office Action.
U.S. Appl. No. 12/684,562, Dec. 28, 2011, Office Action.
U.S. Appl. No. 12/684,569, Dec. 20, 2011, Office Action.
U.S. Appl. No. 12/897,358, Jan. 12, 2012, Notice of Allowance.
U.S. Appl. No. 12/941,809, Dec. 13, 2011, Office Action.
U.S. Appl. No. 12/945,646, Oct. 26, 2011, Office Action.
U.S. Appl. No. 12/955,859, Dec. 15, 2011, Office Action.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 10/435,104, Jan. 12, 2011, Issue Notification.
U.S. Appl. No. 11/113,549, Jan. 4, 2011, Office Action.
U.S. Appl. No. 12/402,398, Jan. 24, 2011, Office Action.
U.S. Appl. No. 12/945,646, Jan. 20, 2011, Office Action.
U.S. Appl. No. 13/017,636, filed Jan. 31, 2011, Carley et al.
U.S. Appl. No. 10/616,832, Jan. 26, 2011, Issue Notification.
U.S. Appl. No. 11/152,562, Jan. 26, 2011, Issue Notification.
U.S. Appl. No. 10/667,144, Feb. 15, 2012, Issue Notification.
U.S. Appl. No. 12/135,858, Feb. 16, 2012, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/608,769, Feb. 10, 2012, Office Action.
U.S. Appl. No. 12/642,319, Feb. 27, 2012, Office Action.
U.S. Appl. No. 12/684,562, Feb. 16, 2012, Office Action.
U.S. Appl. No. 12/724,304, Feb. 10, 2012, Office Action.
U.S. Appl. No. 12/945,646, Feb. 21, 2012, Notice of Allowance.
U.S. Appl. No. 13/039,087, filed Mar. 2, 2011, Palermo et al.
U.S. Appl. No. 11/852,190, Mar. 2, 2011, Office Action.
U.S. Appl. No. 12/122,603, Mar. 3, 2011, Office Action.
U.S. Appl. No. 11/396,731, Mar. 22, 2011, Office Action.
U.S. Appl. No. 11/427,297, Mar. 21, 2011, Office Action.
U.S. Appl. No. 12/135,858, Jul. 13, 2011, Office Action.
U.S. Appl. No. 12/955,859, Jul. 21, 2011, Office Action.
U.S. Appl. No. 10/682,459, Aug. 10, 2011, Issue Notification.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 13/026,989, Sep. 16, 2011, Office Action.
U.S. Appl. No. 12/393,877, Sep. 29, 2011, Office Action.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/941,809, Jan. 30, 2012, Office Action.
U.S. Appl. No. 12/966,923, Feb. 3, 2012, Notice of Allowance.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 11/532,576, Mar. 16, 2011, Issue Notification.
U.S. Appl. No. 12/113,851, Mar. 29, 2012, Office Action.
U.S. Appl. No. 12/114,031, Mar. 6, 2012, Office Action.
U.S. Appl. No. 12/403,277, Apr. 3, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 10/147,774, Apr. 6, 2011, Issue Notification.
U.S. Appl. No. 10/682,459, Apr. 1, 2011, Notice of Allowance.
U.S. Appl. No. 12/403,277, Mar. 31, 2011, Office Action.
U.S. Appl. No. 12/113,851, Apr. 27, 2011, Office Action.
U.S. Appl. No. 12/481,377, Apr. 28, 2011, Office Action.
U.S. Appl. No. 12/122,603, Sep. 23, 2011, Office Action.
U.S. Appl. No. 12/897,358, filed Oct. 4, 2010, Carley.
U.S. Appl. No. 12/961,331, filed Dec. 6, 2010, Voss.
U.S. Appl. No. 12/966,923, filed Dec. 13, 2010, Cummins et al.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996,

(56) References Cited

OTHER PUBLICATIONS pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Advisory Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.

(56) References Cited

OTHER PUBLICATIONS

U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Amendment Under 312.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Office Action.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.

(56) References Cited

OTHER PUBLICATIONS

U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2010, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.

(56) References Cited

OTHER PUBLICATIONS

U.S. Appl. No. 12/403,277, Jul. 8, 2010, Office Action.
U.S. Appl. No. 12/403,277, Oct. 12, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/338,977, Jan. 19, 2012, Office Action.
U.S. Appl. No. 12/684,569, Jan. 27, 2012, Office Action.
U.S. Appl. No. 13/030,922, filed Feb. 18, 2011, Cummins.
U.S. Appl. No. 10/356,214, Feb. 23, 2011, Issue Notification.
U.S. Appl. No. 11/958,281, Mar. 10, 2011, Office Action.
U.S. Appl. No. 13/112,618, filed May 20, 2011, Gianotti et al.
U.S. Appl. No. 13/112,631, filed May 20, 2011, Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 12/481,377, Jun. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 12/122,603, Apr. 22, 2011, Office Action.
U.S. Appl. No. 12/114,091, Apr. 5, 2012, Office Action.
U.S. Appl. No. 11/396,731, Sep. 1, 2011, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/987,792, Sep. 17, 2012, Office Action.
U.S. Appl. No. 13/308,227, filed Nov. 30, 2011, Yibarren.
U.S. Appl. No. 13/525,839, filed Jun. 18, 2012, Carley et al.
U.S. Appl. No. 11/390,586, May 3, 2012, Notice of Allowance.
U.S. Appl. No. 11/427,297, Jun. 26, 2012, Notice of Allowance.
U.S. Appl. No. 12/338,977, Jul. 11, 2012, Office Action.
U.S. Appl. No. 12/393,877, May 21, 2012, Office Action.
U.S. Appl. No. 12/608,773, Jun. 7, 2012, Restriction Requirement.
U.S. Appl. No. 12/608,773, Jul. 20, 2012, Office Action.
U.S. Appl. No. 12/684,542, Apr. 16, 2012, Office Action.
U.S. Appl. No. 12/684,569, Jul. 30, 2012, Office Action.
U.S. Appl. No. 12/688,065, Apr. 26, 2012, Office Action.
U.S. Appl. No. 12/850,242, Aug. 6, 2012, Restriction Requirement.
U.S. Appl. No. 12/941,809, Jun. 1, 2012, Office Action.
U.S. Appl. No. 12/955,859, Aug. 6, 2012, Office Action.
U.S. Appl. No. 13/026,989, Jun. 8, 2012, Office Action.
U.S. Appl. No. 13/039,087, Jul. 17, 2012, Office Action.
U.S. Appl. No. 11/675,462, Aug. 15, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/684,562, Aug. 21, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/402,398, Mar. 13, 2013, Notice of Allowance.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 12/114,091, Nov. 8, 2012, Office Action.
U.S. Appl. No. 12/338,977, Nov. 28, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/608,773, Jan. 7, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 12/961,331, Dec. 4, 2012, Restriction Requirement.
U.S. Appl. No. 13/030,922, Dec. 18, 2012, Restriction Requirement.
U.S. Appl. No. 13/039,087, Nov. 6, 2012, Notice of Allowance.
U.S. Appl. No. 13/490,143, Jan. 4, 2013, Restriction Requirement.
U.S. Appl. No. 12/961,331, Feb. 1, 2013, Office Action.
U.S. Appl. No. 13/488,233, Feb. 5, 2013, Notice of Allowance.
U.S. Appl. No. 10/786,444, Jul. 11, 2013, Notice of Allowance.
U.S. Appl. No. 11/532,325, Jul. 17, 2013, Office Action.
U.S. Appl. No. 13/030,922, Jul. 18, 2013, Office Action.
U.S. Appl. No. 13/525,839, Jul. 15, 2013, Notice of Allowance.
U.S. Appl. No. 13/615,547, Jul. 10, 2013, Issue Notification.
U.S. Appl. No. 11/396,141, Aug. 21, 2013, Office Action.
U.S. Appl. No. 13/026,989, Aug. 23, 2013, Office Action.
U.S. Appl. No. 13/490,143, Aug. 21, 2013, Issue Notification.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 13/898,202, filed May 20, 2013, Walberg et al.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 13/153,594, May 29, 2013, Office Action.
U.S. Appl. No. 13/791,829, May 29, 2013, Office Action.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 13/615,547, Jan. 18, 2013, Office Action.
U.S. Appl. No. 12/106,928, Jun. 28, 2013, Office Action.
U.S. Appl. No. 12/106,937, Jun. 28, 2013, Office Action.
U.S. Appl. No. 12/941,809, Jul. 3, 2013, Office Action.
U.S. Appl. No. 12/961,331, Jul. 3, 2013, Office Action.
U.S. Appl. No. 12/338,977, Jun. 19, 2013, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 14/539,830, filed Nov. 12, 2014, Clark.
U.S. Appl. No. 14/562,467, filed Dec. 5, 2014, Ellingwood et al.
U.S. Appl. No. 11/113,549, Mar. 14, 2014, Notice of Allowance.
U.S. Appl. No. 11/396,141, Nov. 4, 2013, Notice of Allowance.
U.S. Appl. No. 11/411,925, Oct. 1, 2013, Office Action.
U.S. Appl. No. 11/411,925, Feb. 5, 2014, Notice of Allowance.
U.S. Appl. No. 11/455,993, Jan. 29, 2014, Office Action.
U.S. Appl. No. 11/455,993, Aug. 11, 2014, Notice of Allowance.
U.S. Appl. No. 11/532,325, Dec. 2, 2013, Office Action.
U.S. Appl. No. 11/532,325, Jan. 16, 2015, Notice of Allowance.
U.S. Appl. No. 11/674,930, Apr. 3, 2014, Notice of Allowance.
U.S. Appl. No. 11/852,190, Nov. 26, 2013, Office Action.
U.S. Appl. No. 11/852,190, Feb. 12, 2014, Notice of Allowance.
U.S. Appl. No. 11/958,295, Jun. 13, 2014, Notice of Allowance.
U.S. Appl. No. 12/106,928, Dec. 2, 2013, Office Action.
U.S. Appl. No. 12/106,928, Mar. 25, 2014, Advisory Action.
U.S. Appl. No. 12/106,928, Oct. 3, 2014, Notice of Allowance.
U.S. Appl. No. 12/106,937, Jan. 22, 2014, Office Action.
U.S. Appl. No. 12/113,851, Mar. 17, 2014, Office Action.
U.S. Appl. No. 12/113,851, Aug. 21, 2014, Office Action.
U.S. Appl. No. 12/114,031, Mar. 10, 2014, Office Action.
U.S. Appl. No. 12/114,091, Feb. 12, 2015, Office Action.
U.S. Appl. No. 12/122,603, Nov. 20, 2013, Office Action.
U.S. Appl. No. 12/122,603, Apr. 30, 2014, Office Action.
U.S. Appl. No. 12/393,877, Aug. 4, 2014, Notice of Allowance.
U.S. Appl. No. 12/403,277, Jan. 27, 2014, Office Action.
U.S. Appl. No. 12/403,277, Aug. 15, 2014, Office Action.
U.S. Appl. No. 12/548,274, Aug. 14, 2014, Office Action.

(56) References Cited

OTHER PUBLICATIONS

U.S. Appl. No. 12/608,773, Jul. 17, 2014, Office Action.
U.S. Appl. No. 12/642,319, Dec. 16, 2013, Office Action.
U.S. Appl. No. 12/642,319, May 27, 2014, Notice of Allowance.
U.S. Appl. No. 12/684,470, Jun. 4, 2014, Office Action.
U.S. Appl. No. 12/684,470, Nov. 14, 2014, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Sep. 10, 2014, Office Action.
U.S. Appl. No. 12/684,562, Feb. 17, 2015, Notice of Allowance.
U.S. Appl. No. 12/684,569, Apr. 23, 2014, Office Action.
U.S. Appl. No. 12/688,065, Oct. 18, 2013, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/941,809, Nov. 8, 2013, Office Action.
U.S. Appl. No. 12/941,809, Feb. 3, 2014, Notice of Allowance.
U.S. Appl. No. 12/950,628, Apr. 25, 2014, Notice of Allowance.
U.S. Appl. No. 12/961,331, Sep. 20, 2013, Advisory Action.
U.S. Appl. No. 12/961,331, Apr. 25, 2014, Notice of Allowance.
U.S. Appl. No. 12/987,792, Jan. 21, 2014, Office Action.
U.S. Appl. No. 12/987,792, Jun. 11, 2014, Office Action.
U.S. Appl. No. 12/987,792, Aug. 25, 2014, Notice of Allowance.
U.S. Appl. No. 13/030,922, Jan. 8, 2014, Notice of Allowance.
U.S. Appl. No. 13/112,618, Nov. 20, 2013, Office Action.
U.S. Appl. No. 13/112,618, Dec. 15, 2014, Office Action.
U.S. Appl. No. 13/112,631, Dec. 2, 2013, Office Action.
U.S. Appl. No. 13/112,631, Nov. 20, 2014, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/222,899, Jul. 31, 2014, Office Action.
U.S. Appl. No. 13/308,227, Sep. 11, 2013, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 13/898,202, Aug. 21, 2014, Office Action.
U.S. Appl. No. 13/898,202, Feb. 10, 2015, Notice of Allowance.
U.S. Appl. No. 14/017,039, Jan. 23, 2015, Office Action.
U.S. Appl. No. 11/396,731, Feb. 12, 2015, Office Action.
U.S. Appl. No. 12/106,937, Mar. 5, 2015, Notice of Allowance.
U.S. Appl. No. 12/113,851, Feb. 20, 2015, Notice of Allowance.
U.S. Appl. No. 12/122,603, Apr. 9, 2015, Office Action.
U.S. Appl. No. 12/608,773, Mar. 12, 2015, Office Action.
U.S. Appl. No. 13/112,631, Apr. 15, 2015, Office Action.
U.S. Appl. No. 13/222,899, Apr. 1, 2015, Office Action.
U.S. Appl. No. 11/396,731, Jul. 9, 2015, Notice of Allowance.
U.S. Appl. No. 11/532,325, Jul. 8, 2015, Issue Notification.
U.S. Appl. No. 12/114,091, Jul. 23, 2015, Office Action.
U.S. Appl. No. 12/684,562, Jul. 8, 2015, Issue Notification.
U.S. Appl. No. 13/112,618, May 18, 2015, Office Action.
U.S. Appl. No. 13/308,227, Jul. 14, 2015, Office Action.
U.S. Appl. No. 13/791,846, Jun. 4, 2015, Office Action.
U.S. Appl. No. 13/908,796, Jul. 21, 2015, Office Action.
U.S. Appl. No. 14/017,039, Jun. 10, 2015, Office Action.
U.S. Appl. No. 14/466,576, Jul. 8, 2015, Office Action.
U.S. Appl. No. 13/222,899, Aug. 5, 2015, Office Action.
U.S. Appl. No. 14/023,428, Jul. 27, 2015, Office Action.
U.S. Appl. No. 14/077,007, Jul. 27, 2015, Office Action.
U.S. Appl. No. 14/246,926, Aug. 5, 2015, Office Action.

\* cited by examiner

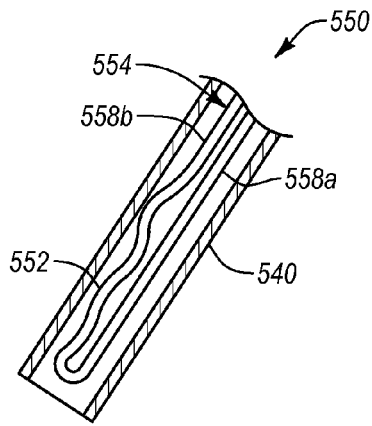
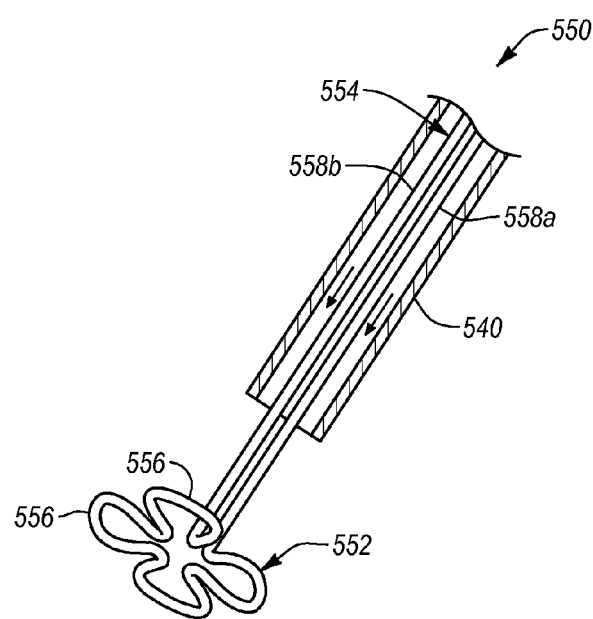
Fig. 5A    Fig. 5B
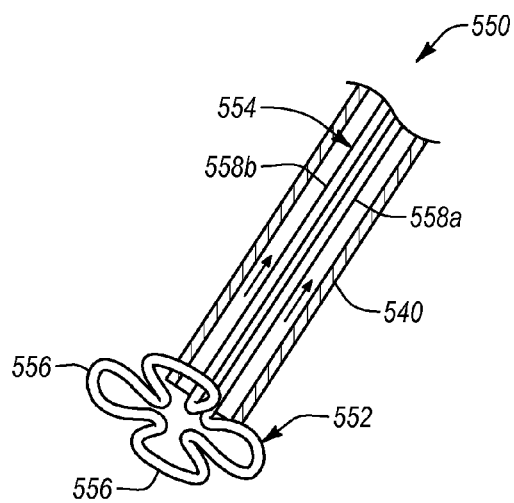
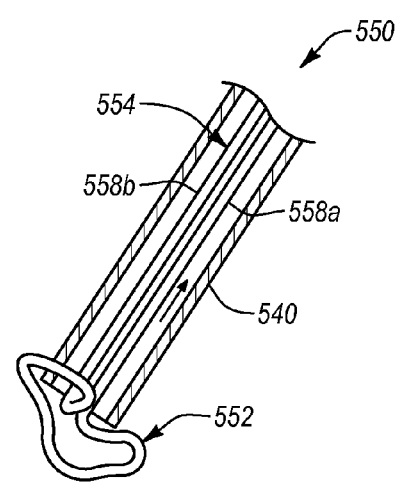
Fig. 5C    Fig. 5D

CLOSURE DEVICES, SYSTEMS, AND METHODS

This patent application claims the benefit of and priority to U.S. Provisional Patent Application Ser. No. 61/143,751, entitled "Vessel Closure Devices and Methods," filed Jan. 9, 2009, the disclosure of which is incorporated herein by reference in its entirety.

BACKGROUND

1. Technical Field

The present disclosure relates generally to medical devices and their methods of use. In particular, the present disclosure relates to vessel closure systems and devices and corresponding methods of use.

2. The Technology

Catheterization and interventional procedures, such as angioplasty or stenting, generally are performed by inserting a hollow needle through a patient's skin and tissue into the vascular system. A guidewire may be advanced through the needle and into the patient's blood vessel accessed by the needle. The needle is then removed, enabling an introducer sheath to be advanced over the guidewire into the vessel, e.g., in conjunction with or subsequent to a dilator.

A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally, external pressure would be applied to the puncture site until clotting and wound sealing occur; however, the patient must remain bedridden for a substantial period after clotting to ensure closure of the wound. This procedure may also be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs. Although some closure systems may be available, they provide limited control to flexibility to the operator, which may lead to improper or undesirable closure of the puncture site.

BRIEF SUMMARY

The present disclosure can include a closure system. In one embodiment, the closure system can include a handle member, a tube set, an inner lumen disposed at least partially within the tube set, a plunger member movably coupled to the handle member, and an anchor member at least partially disposed within the inner lumen. In a further embodiment, the anchor member can include an anchor portion and an elongate portion. The anchor portion can be disposed in the inner lumen in an initial configuration and configured to move to an expanded configuration once deployed from the inner lumen.

The present disclosure can also include a method of closing a body lumen opening. In one embodiment, the method can include advancing a closure system at least partially into a body lumen opening. The closure system can include a handle member, a tube set configured to deliver and/or deploy a closure element, an inner lumen disposed at least partially within the tube set, a plunger member movably coupled to the handle member, and an anchor member at least partially disposed within the inner lumen. In a further embodiment, the anchor member can include an anchor portion and an elongate portion, the anchor portion being disposed in the inner lumen in an initial configuration and configured to move to an expanded configuration once deployed from the inner lumen. The method can also include deploying the anchor portion of the anchor member within the body lumen. In further embodiments, the method can include positioning the anchor portion of the anchor member against a distal surface of the lumen wall proximate the body lumen opening. In yet further embodiments, the method can include advancing the tube set in a distal direction to position the distal end of the tube set against a proximal surface of the lumen wall proximate the body lumen opening. In addition, the method can include deploying a closure element into the lumen wall proximate the body lumen opening to close the body lumen opening.

In a yet further embodiment, the present disclosure can include an anchor member. In one embodiment, the anchor member can include an elongate portion having a distal end and proximal end. In addition, the anchor member can include an anchor portion coupled to the distal end of the elongate portion. In a yet further embodiment, the anchor portion is configured to move elastically between an initial configuration and an expanded configuration. The expanded configuration can include a plurality of projections.

These and other advantages and features of the present disclosure will become more fully apparent from the following description and appended claims, or may be learned by the practice of the disclosure as set forth hereinafter.

BRIEF DESCRIPTION OF THE DRAWINGS

To further clarify at least some of the advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIGS. 5A-5D disclose an example method of operating the anchor member of FIGS. 3A-3B in accordance with one embodiment;

It should be noted that the figures are not drawn to scale and that elements of similar structures or functions are generally represented by like reference numerals for illustrative purposes throughout the figures. It also should be noted that the

DETAILED DESCRIPTION

The present disclosure relates to devices, systems, and methods for closing an opening in a body lumen. In one example embodiment, a closure system of the present disclosure may allow an operator to quickly and efficiently close a body lumen opening while simultaneously providing the operator with a greater measure of control and flexibility in positioning and anchoring the closure system than previously available. For example, the closure system may allow an operator to achieve a more intimate securement of a closure element in the tissue surrounding a body lumen opening. In a yet further embodiment, the closure system may be compatible with a wider range of body lumen wall thicknesses, thereby taking into account the possibility of calcifications or scar tissue in the lumen wall. In addition, the closure system may be configured to advance into a body lumen opening over a guidewire. Furthermore, the closure system may be compatible with a variety of sizes of body lumen openings and tissue tracts.

Embodiments of the disclosure further relate to a device closure system with a removable anchor. In one example, the anchor can be deployed from a contracted state to an expanded state. When in the expanded state, the anchor can be used to locate an opening in a vessel (e.g., an arteriotomy) when deploying, for example, a closure element, such as a clip or staple. The anchor, in conjunction with a tube set in the closure system, may sandwich the tissue surrounding the opening in the vessel. This effectively locates the opening and aids in effective and proper deployment of the closure element.

The closure system may then retract or remove the anchor during use of the closure system, leaving the arteriotomy or opening at least substantially closed or sealed by the closure element. During removal, the anchor can deform without dislodging the closure element. More specifically in one embodiment, the anchor is withdrawn back into the tube set and into the pre-deployed state. Thus, the closure system and close an opening in a body lumen using a removable anchor.

Figure 1:
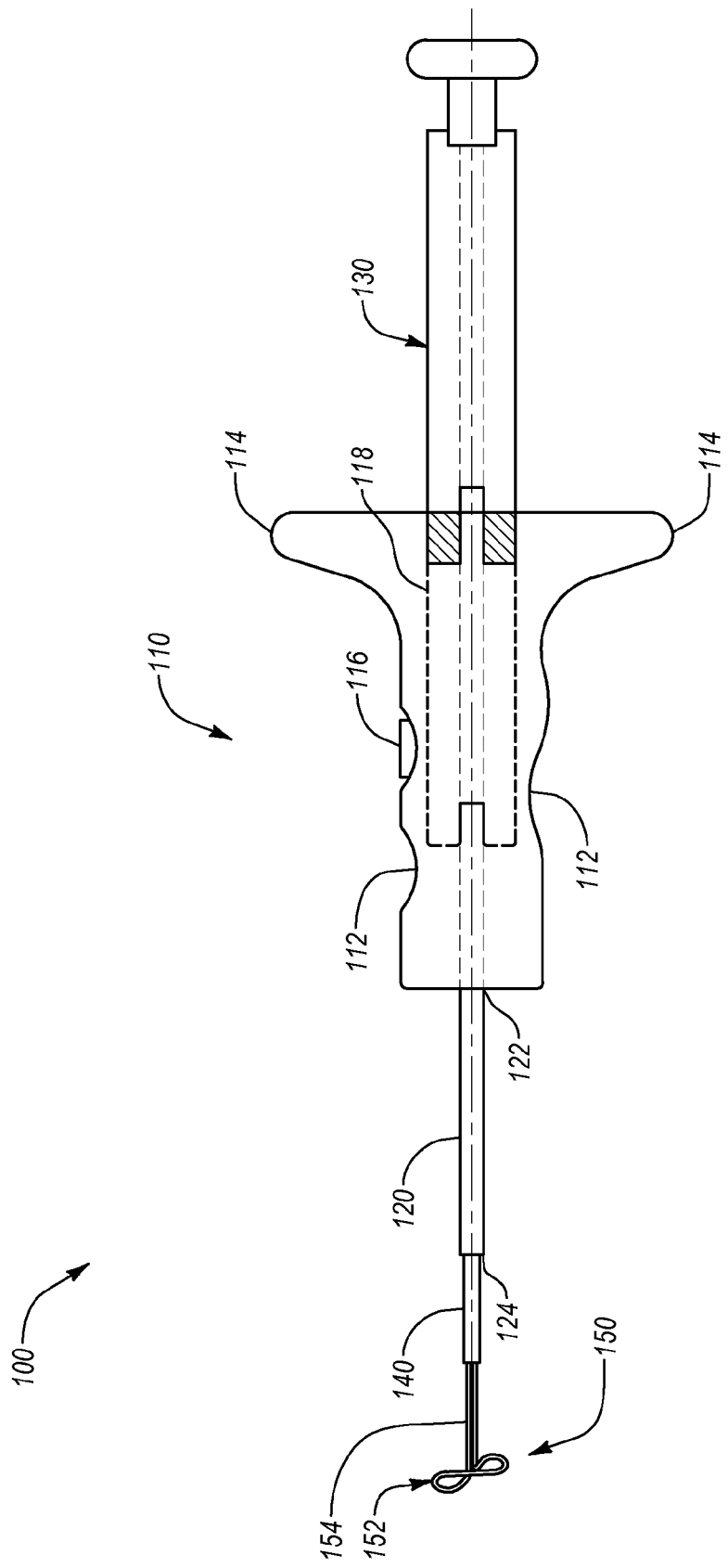
FIG. 1 discloses a closure system in accordance with one example embodiment.

Reference is now made to FIG. 1 which illustrates a closure system 100 in accordance with an implementation of the present disclosure. The closure system 100 may be configured to close an opening in a body lumen. The closure system 100 may include a handle member 110, a tube set 120 coupled to the handle member 110, a plunger member 130, an inner lumen 140, and an anchor member 150 disposed at least partially within the inner lumen 140. An operator, such as a physician, may utilize the closure system 100 and the elements thereof to close an opening in a body lumen. For example, as will be explained in more detail below, the plunger member 130 may be used to deploy the anchor member 150 to locate the distal surface of a lumen wall and position the closure system 100 relative to a body lumen opening. Thereafter, the handle member 110 and tube set 120 may be used to deliver a closure element, such as a clip or staple, and deploy the closure element into the tissue of the body lumen wall to close or substantially close the body lumen opening.

The handle member 110 of the closure system 100 may be configured to assist an operator, such as a physician, to grip, manipulate, advance, and/or operate the closure system 100 in order to close a body lumen opening. In particular, the handle member 110 may have a shape and size that conforms to the shape and size of a human hand. The handle member 110 may also include a number of indentations 112 configured to at least partially receive the fingers and/or thumbs of the operator. The indentations 112 may assist the operator to grip and manipulate the handle member 110 and closure system 100. The handle member 110 may also include one or more flanges 114 to assist an operator to grip, advance, and/or retract the handle member 110 and/or closure system 100.

The handle member 110 may also include any number of mechanisms necessary to deploy a closure element. For example, the handle member 110 may include a button 116 operatively associated with one or more mechanisms configured to deploy a closure element. The button 116 may be positioned in or proximate to one of the one or more indentations 112. In a further embodiment, the button 116 may be operatively associated with one or more elements of the tube set 120 configured to deploy the closure element 100. As a result, an operator may depress the button 116 in order to push, fire, or eject a closure element from the tube set 120 into the tissue of a body lumen to close a body lumen opening.

In a further embodiment, the handle member 110 may include a recess 118 configured to receive at least a portion of the plunger member 130. The recess 118 may be further configured to allow the plunger member 130 to move in a longitudinal direction relative to the handle member 110. In particular, the recess 118 may allow the plunger member 130 to move both distally and proximally relative to the handle member 110. For example, the recess 118 may have a cross-sectional shape similar to, but slightly larger than, the cross sectional shape of the plunger member 130. As a result, the plunger member 130 may slide into and out of the recess 118 to move relative to the handle member 110.

The handle member 110 may include any number of rigid or semi-rigid materials. For example, the handle member 110 may include any number of polymers, plastics, metals, composites, other similar materials, or combinations thereof.

The tube set 120 may be coupled to and/or partially disposed within the handle member 110. The tube set 120 may have a proximal end 122 coupled to the handle member 110 and opposite a distal end 124. The tube set 120 may be configured to contain, deliver, and/or deploy a closure element. In particular, the tube set 120 may include one or more tubular members and/or other mechanisms configured to house, advance, push, fire, and/or eject the closure element. For example, the tube set 120 may include a pusher tube, a garage tube, a carrier tube, and/or other similar elements. In one embodiment, the tube set 120 may include a spring-loaded pusher member configured to deploy the closure element when released or activated. Some example tube sets are disclosed in FIGS. 7-8 and described in more detail below.

The closure element may be disposed within the tube set 120 in an initial, open configuration and may be configured to be deployed from the tube set 120 and move to a deployed, closed configuration. In particular, in one embodiment, the closure element may store sufficient energy, while in its initial, open configuration, to engage the tissue of and close an opening in a lumen wall. For example, the closure element may include any of a number of shape memory and/or superelastic materials and may be set to elastically return to a deployed, closed configuration from any other configuration. In one embodiment, the closure element may include nitinol. In a further embodiment, the closure element may be a clip, staple, or other closure element.

The closure system 100 may also include an inner lumen 140. The inner lumen 140 may be disposed at least partially within the tube set 120, the handle member 110, and/or the plunger member 130. In a further implementation, the inner lumen 140 may be movable, such as slidable, with respect to the tube set 120, the handle member 110, and/or the plunger member 130. As a result, the inner lumen 140 may move either distally or proximally relative to the tube set 120, the handle member 110, and/or the plunger member 130.

The inner lumen 140 may be configured to house and deliver the anchor member 150 to or away from a body lumen opening. In a further embodiment, the inner lumen 140 may be integrated into or replaced by an element of the tube set 120. The inner lumen 140 may include any number of flexible or semi-rigid materials. For example, the inner lumen may include one or more polymers, elastomers, plastics, metals, composites, other similar materials, or combinations thereof.

As introduced above, the closure system 100 may include an anchor member 150. The anchor member 150 may be configured to locate, position the closure system 100 relative to, and/or anchor the tissue surrounding a body lumen opening. The anchor member 150 may include an anchor portion 152 and an elongate portion 154. The anchor portion 152 may be configured to be positioned and/or anchored against the distal surface of a lumen wall. The elongate portion 154 may be coupled to the anchor portion 152 and may be configured to control, deploy, position, stabilize, and/or retract the anchor portion 152. In particular, the elongate portion 154 may extend away from the anchor portion 152 in a proximal direction through the inner lumen 140, the tube set 120, the handle member 110, and/or the plunger member 130. In a further embodiment, the elongate portion 154 may be coupled at its proximal end 122 to the plunger member 130. In a yet further embodiment, the elongate portion 154 may be selectively detachable from and recouplable to the plunger member 130.

The anchor portion 152 of the anchor member 150 may be disposed in an initial, contracted configuration within the inner lumen 140. The elongate portion 154 of the anchor member 150 may extend proximally from the anchor portion 152 to the plunger member 130. In addition, the elongate portion 154 may transfer forces from the plunger member 130 to the anchor portion 152. Accordingly, by advancing the plunger member 130 or elongate portion 154 in a distal direction relative to the inner lumen 140 an operator may deploy the anchor portion 152 of the anchor member 150 from the distal end of the inner lumen 140. Retracting the plunger member 130 in a proximal direction may position and/or anchor the anchor portion 152 against a distal surface of a lumen wall. In a further embodiment, further refracting the plunger member 130 in a proximal direction may retract the anchor portion 152 of the anchor member 150 from the body lumen and/or into the inner lumen 140 or tube set 120.

The anchor portion 152 of the anchor member 150 may be configured to move from an initial, contracted configuration within the inner lumen 140 to a deployed, expanded configuration once deployed from the inner lumen 140. To facilitate movement from an initial, contracted configuration to a deployed, expanded configuration, the anchor portion 152 of the anchor member 150 may include one or more superelastic or shape memory materials such as shape memory alloys. For example, and as will be explained in more detail below, the anchor portion 152 be heat set in a deployed, expanded configuration. The anchor portion 152 may then be elastically deformed into an initial, contracted configuration contracted and disposed within the inner lumen 140. In its initial, contracted configuration, the anchor portion 152 may store sufficient energy to return to its deployed, expanded configuration once released from the inner lumen 140.

In one embodiment, a user may operate the plunger member 130 to deploy and/or retract the anchor member 150. For example, the plunger member 130 may be configured to at least partially receive the tube set 120 and/or the inner lumen 140. In a further embodiment, the plunger member 130 may also be configured to receive a portion of the anchor member 150 and/or a guidewire. In a further embodiment, the inner lumen 140 and/or anchor member 150 may be coated to minimize friction within the inner lumen 140 to ease deployment.

The proximal end 122 of the plunger member 130 may be configured to be gripped and/or operated by an operator such as a physician. For example, an operator may grip the handle member 110 with a first hand and grip the proximal end of the plunger member 130 with a second hand in order to advance or retract the plunger member 130 relative to the handle member 110. As a result, the operator may deploy the anchor portion 152 of the anchor member 150 from the inner lumen 140 and/or position the anchor portion 152 against a distal surface of a lumen wall thereby locating the body lumen opening to be closed.

Thereafter, the operator may advance the handle member 110 in a distal direction relative to the plunger member 130 and inner lumen 140 to position the distal end 124 of the tube set 120 against a proximal surface of the lumen wall. By so doing, the operator may facilitate the closure of the body lumen opening by at least partially gripping, sandwiching, and/or immobilizing the tissue surrounding the body lumen opening. The operator may then deploy a closure element into the tissue of the lumen wall to close the body lumen opening.

The shape of the plunger member 130 may correspond with the shape of the recess 118 to facilitate relative movement between the handle member 110 and the plunger member 130. For example, the cross sectional shape of both the plunger member 130 and the recess 118 may be any shape desired such as circular, triangular, rectangular, or other shapes, or combinations thereof. In addition, the length of the plunger member 130 and the corresponding depth of the recess 118 may be any length and depth desired to allow sufficient relative movement between the plunger member 130 and handle member 110. For example, the length of the plunger member 130 and the corresponding depth of the recess 118 may be sufficient to allow deployment of the anchor portion 152 from the inner lumen.

In a further embodiment, the closure system 100 may include a self-tensioning mechanism configured to automatically provide tension in the anchor member 150 once the anchor portion 152 has deployed. For example, in one embodiment, the handle member 110 may include a spring mechanism disposed in the recess 118 and configured to resist and/or counteract movement of the plunger member 130 in a distal direction relative to the handle member 110. In particular, advancing the plunger member 130 in a distal direction relative to the handle member 110 may transfer energy to the spring mechanism, which may be released once the operator releases the plunger member 130.

As a result, the spring mechanism may move the plunger member 130 in a proximal direction relative to the handle member 110 thereby retracting the anchor portion 152 in a proximal direction, thereby automatically engaging the distal surface of a lumen wall, and/or advancing the handle member 110 and tube set 120 in a distal direction, thereby engaging the proximal surface of the lumen wall. The spring mechanism can also create sufficient tension within the anchor member 150 to produce a desired pressure on the tissue of the lumen wall between the anchor portion 152 and the tube set 120. Accordingly, the closure system 100 may automatically and efficiently create the desired sandwiching or immobilizing force on the tissue surrounding the body lumen opening. In addition, the spring mechanism may make it unnecessary for the operator to provide the movement or force necessary to position the closure system 100 relative to the body lumen opening. In additional embodiments, any other self-tensioning mechanism may be included in the closure system 100 to produce to desired tension in the anchor member 150 and force upon the tissue surrounding the body lumen opening. In a yet further embodiment, the plunger member 130 and closure system 100 may have a click or ratchet function similar to that of a "click" pen.

In a yet further embodiment, the closure system 100, or the elements thereof, may include a mechanism for determining the thickness of a lumen wall and/or the distance between the anchor portion 152 and the distal end 124 of the tube set 120. For example, the plunger member 130 may have a plurality of indicator lines along the length thereof. The indicator lines may be positioned and marked to indicate the position of the deployed anchor portion 152 relative to the distal end 124 of the tube set 120. In particular, the number of indicator lines exposed as the plunger member 130 is retracted may indicate the thickness of the tissue surrounding the body lumen opening being closed. The indicator lines may be calibrated so that they read zero thickness when the anchor portion 152 is position directly against the distal end 124 of the tube set 120. As a result, the operator may refer to the indicator lines to determine the position of the anchor portion 152 relative to the distal end 124 of the tube set 120 and/or the thickness of the tissue surrounding a body lumen opening.

Additionally, the closure system 100 may incorporate at least one component of the closure systems 600 and 800, tube sets 720 and 820, and anchor members 350, 450, 550, and 650 described in connection with FIGS. 3-6G, respectively.

Figure 2A:
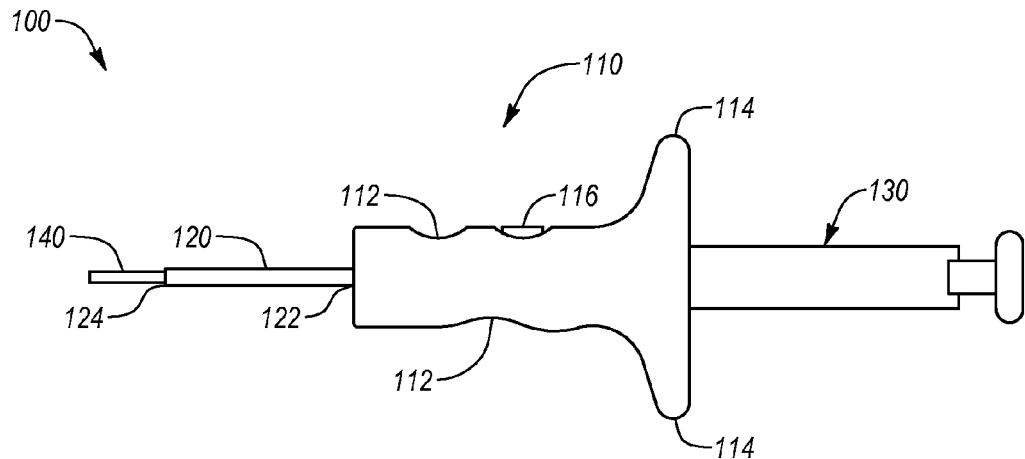
FIGS. 2A-2D disclose an example method of operating the closure system of FIG. 1 in accordance with a further embodiment.
Figure 2B:
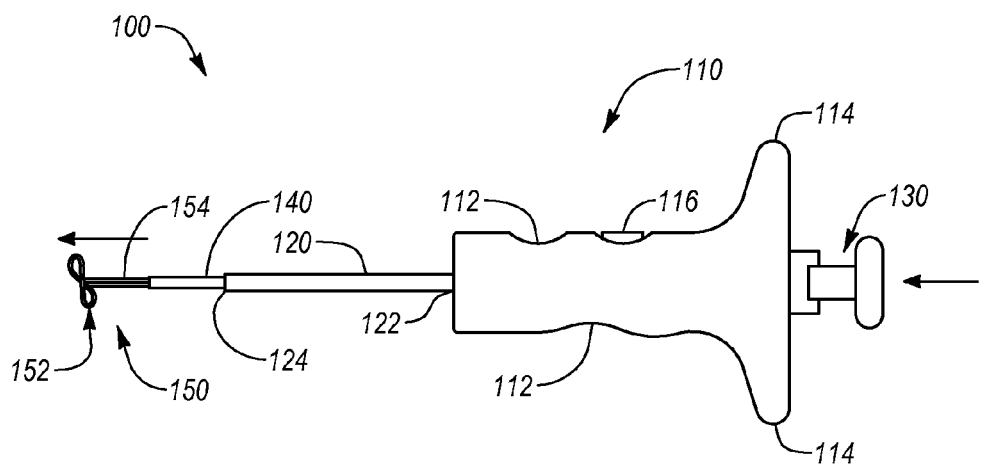

Reference is now made to FIGS. 2A-2D, which illustrate an example method of operating the closure system 100 of FIG. 1. In particular, FIG. 2A illustrates the closure system 100 in an initial configuration. In this initial configuration, the plunger member 130 may be fully retracted relative to the handle member 110, and the anchor portion 152 of the anchor member 150 may be disposed within the inner lumen 140. Advancing the plunger member 130 in a distal direction relative to the handle member 110, the tube set 120, and the inner lumen 140 may deploy the anchor portion 152 of the anchor member 150 from the inner lumen 140, as shown in FIG. 2B. As a result, the anchor portion 152 may move from an initial, contracted configuration to a deployed, expanded configuration. In a further implementation, the plunger member 130 may include two or more plunger components. For example, the plunger member 130 may include a first component configured to deploy and/or retract the anchor member 150 and a second component configured to advance and/or retract the inner lumen 140. In a yet further implementation, the first and second components of the plunger member 130 may be movable with respect to one another.

Figure 2C:
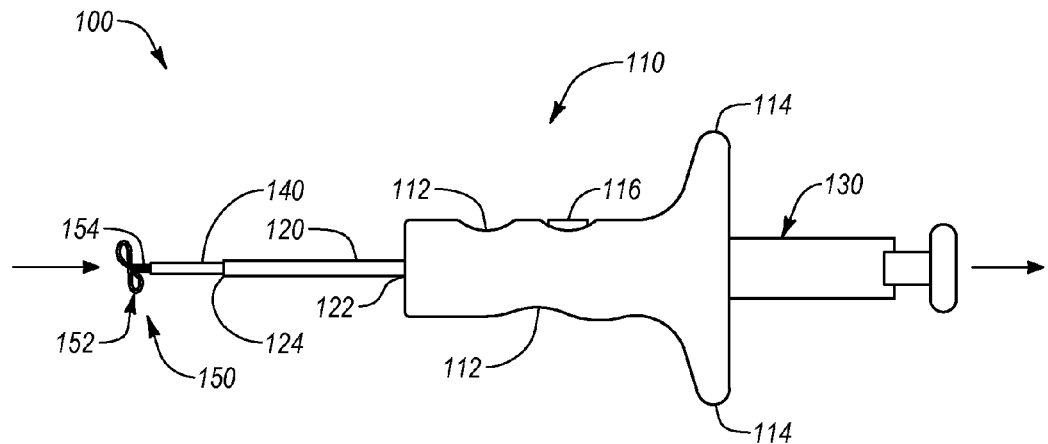
Figure 2D:
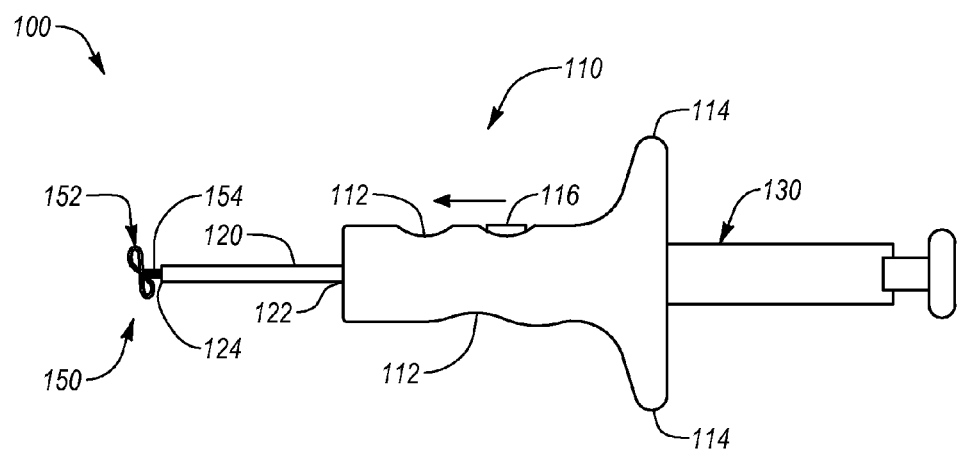

Thereafter, retracting the plunger member 130 in a proximal direction relative to the handle member 110, the tube set 120, and/or the inner lumen 140 may retract the anchor portion 152 in a proximal direction, as shown in FIG. 2C. As shown in FIG. 2D, advancing the handle member 110 in a distal direction relative to the plunger member 130 may advance the tube set 120 in a distal direction until the distal end 124 of the tube set 120 is proximate the anchor portion 152 of the anchor member 150. As a result, an operator of the closure system 100 may locate, anchor, and/or immobilize the tissue surrounding a body lumen opening between the tube set 120 and anchor portion 152. Thereafter, the operator may deploy a closure element into the body lumen surrounding the body lumen opening to close the body lumen opening.

Figure 3A:
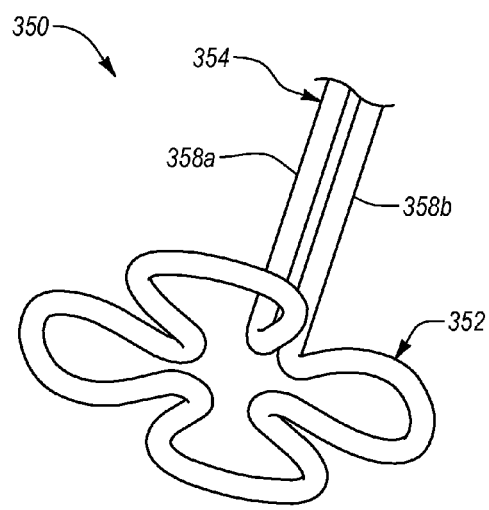
FIGS. 3A-3B disclose an example anchor member in accordance with a yet further embodiment.
Figure 3B:
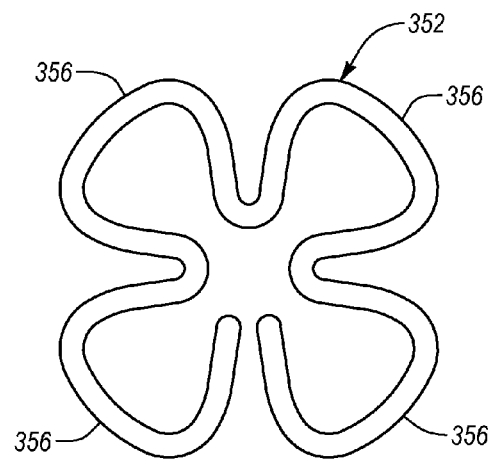

Reference is now made to FIGS. 3A-3B, which disclose an example anchor member 350 in accordance with implementations of the present disclosure. The example anchor member 350 of this configuration may be functionally similar to the example anchor member 150 previously described above and shown in FIGS. 1-2D in most respects, wherein certain features will not be described in relation to this configuration wherein those components may function in the manner as described above and are hereby incorporated into this additional configuration described below. Like structures and/or components are given like reference numerals. Additionally, the anchor member 350 may incorporate at least one component of the anchor members 450, 550, and 650 described in connection with FIGS. 4-6G, respectively.

The anchor member 350 may be configured to assist an operator to locate, anchor, immobilize, and/or support a body lumen opening and/or the surrounding tissue of the lumen wall. The anchor member 350 may include an anchor portion 352 and an elongate portion 354. The anchor portion 352 may include any size and/or shape configured to anchor against a surface of a lumen wall or to locate a body lumen opening. For example, the anchor portion may include a plurality of projections 356 configured to engage the tissue of a lumen wall. The projections 356 may be shaped, positioned, and/or oriented in any configuration desired to provide positioning or anchoring support. The anchor portion 352 may include any number of projections 356 desired. In the embodiment shown in FIGS. 3A-3B the anchor portion 352 of the anchor member 350 includes four projections 356, however, the anchor portion 352 may have fewer or more projections 356 than four.

In one embodiment, the projections may extend in a direction or a plane substantially perpendicular to the longitudinal axis of the elongate portion 354. In one configuration, the projections 356 may be rounded. In particular, the projections 356 may be leaf-shaped or pedal-shaped. In a further embodiment, the anchor portion 352 may have a shape substantially similar to a four leaf clover.

The anchor portion 352 may be coupled to the distal end of the elongate portion 354. The elongate portion 354 may include one or more elongate members 358. The elongate member(s) 358 may be configured to advance, retract, position, and/or deploy the anchor portion 352. In particular, the elongate member(s) 358 may be longitudinally rigid or semirigid to facilitate advancing or retracting the anchor portion 352. In one embodiment, the elongate member(s) 358 may have a solid configuration such as a nitinol wire or a mandrel. In further embodiments, the elongate member(s) 358 may have a generally tubular configuration.

The anchor portion 352 and/or elongate portion 354 may include any number of materials. In one embodiment, the anchor portion 352 may include the same materials as the elongate portion 354. In a further embodiment, the anchor portion 352 may include different materials than the elongate portion 354.

In one embodiment, the anchor portion 352 and elongate portion 354 may include a single shape memory or superelastic wire forming both the elongate portion 354 and the anchor portion 352. The wire may be set into any shape desired for the elongate portion 354 and anchor portion 352. In particular, the wire may be set in an elongate form for the elongate portion 354 and may be set with a plurality of bights or beds forming the expanded form of the anchor portion 352. As shown in FIGS. 3A-3B, in one configuration, the wire may form a plurality of projections 356.

The anchor portion 352 may be configured to elastically deform to any shape and then return to its expanded shape illustrated FIGS. 3A-3B once released. For example, the anchor portion 352 may be elastically deformed into an elongate and/or contracted configuration and disposed within a lumen. While in this contracted configuration, the anchor portion 352 may store sufficient energy to return to its expanded configuration. Once the anchor portion 352 is deployed from the lumen, the anchor portion 352 may release the stored energy and return to its expanded configuration.

In a further embodiment, the anchor portion 352 of the anchor member 350 may include one or more gripping elements along a proximal surface. The gripping elements may be configured to provide a frictional or immobilizing force on tissue surrounding a body lumen opening. For example, the anchor portion 352 may include a plurality of ridges or teeth along a proximal surface configured to engage and grip or immobilize the tissue surrounding a body lumen opening.

Figure 4A:
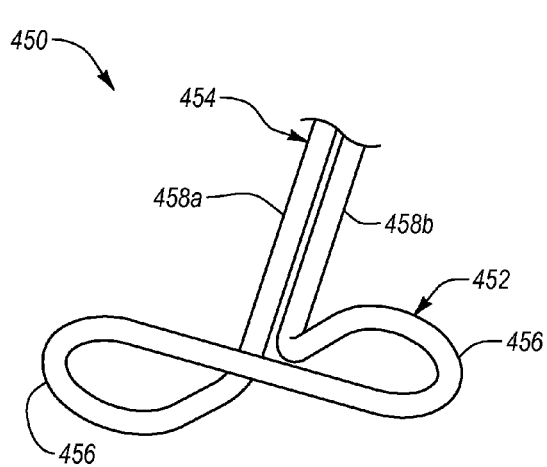
FIGS. 4A-4B disclose an example anchor member in accordance with an additional example embodiment.
Figure 4B:
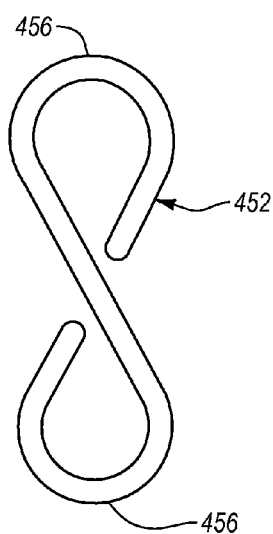

Reference is now made to FIGS. 4A-4B, which illustrate an additional anchor member 450 in accordance with a further embodiment of the present disclosure. The example anchor member 450 of this configuration may be functionally similar to the example anchor members 150 and 350 previously described above and shown in FIGS. 1-3B in most respects, wherein certain features will not be described in relation to this configuration wherein those components may function in the manner as described above and are hereby incorporated into this additional configuration described below. Like structures and/or components are given like reference numerals. Additionally, the anchor member 450 may incorporate at least one component of the anchor members 550 and 650 described in connection with FIGS. 5A-6G, respectively.

In one embodiment, the anchor member 450 may include an anchor portion 452 and an elongate portion 454. The anchor portion 452 may include a plurality of projections 456 extending substantially perpendicular to the longitudinal axis of the elongate portion 454. As shown, the anchor portion 452 may include a figure-8 shape having two projections 456. However, the anchor portion 452 may be configured to have any desired shape and/or size having any number of projections.

The elongate portion 454 may include one or more elongate members 458. In one embodiment, the elongate member(s) 458 and anchor portion 452 may be part of a single continuous piece of shape memory or superelastic wire. For example, the wire may extend along the elongate portion 454 and may form the projections 456 of the anchor portion 452 and then may terminate or alternatively extend again along the elongate portion 454. In a further embodiment, portions of the wire may overlap itself or cross over in forming the anchor portion 452. The overlaps or crosses of the wire may provide better resistance against collapse or more support to the anchor portion 452.

Reference is now made to FIGS. 5A-5D, which illustrate a method of deploying and retracting an anchor member 550. The example anchor member 550 of this configuration may be functionally similar to the example anchor members 150, 350, and 450 previously described above and shown in FIGS. 1-4B in most respects, wherein certain features will not be described in relation to this configuration wherein those components may function in the manner as described above and are hereby incorporated into this additional configuration described below. Like structures and/or components are given like reference numerals. Additionally, the anchor member 550 may incorporate at least one component of the anchor member 650 described in connection with FIGS. 6A-6G.

In particular, FIG. 5A illustrates the anchor member 550 disposed within a lumen 540 in an initial, contracted configuration. As shown, the anchor member 550 may include an elongate portion 554 and an anchor portion 552. The elongate portion 554 may include a plurality of elongate members 558, such as a first elongate member 558A and a second elongate member 558B.

As shown in FIG. 5B advancing the elongate portion 554, such as one or both of the elongate members 558, in a distal direction relative to the lumen 540 may deploy the anchor portion 552 from the distal end of the lumen 540. As a result, the anchor portion 552 may move from an initial, contracted configuration to a deployed, expanded configuration. In one embodiment, the deployed, expanded configuration may include a plurality of projections 556. In a further embodiment, retracting the elongate portion 554 in a proximal direction may provide an anchoring force. For example, retracting the elongate members 558 may anchor the anchor portion 552 against the distal surface of a lumen wall or any other surface against which the anchor portion 552 is positioned, as shown in FIG. 5C. In one embodiment, retracting both elongate members 558 simultaneously may produce tension or some other force in the anchor portion 552 which may increase the resistance of the anchor portion 552 to contracting. For example, the tension of both elongate members 558 may be simultaneously transferred to the anchor portion 552 thereby creating sufficient tension in the anchor portion 552 to resist movement by the anchor portion 552 away from its expanded configuration. In addition, providing an opposing force against a proximal surface of the anchor portion 552, such as with the lumen wall, may also assist in creating sufficient tension in the anchor portion 552 to resist contraction of the anchor portion 552. In a further implementation, the wires of the anchor portion 552 may overlap or cross over each other in order to increase resistance.

As shown in FIG. 5D, retracting only one elongate member, such as the first elongate member 558A, may lessen the tension in the anchor portion 552, thereby allowing the anchor portion to move from its deployed, expanded configuration to a contracted configuration. As a result, by retracting only the first elongate member 558A, without applying tension to the second elongate member 558B or with applying a distal force to the second elongate member 558B, the anchor portion 552 may contract and be retracted into the lumen 540. In further implementations, by retracting only the second elongate member 558B, without applying tension to the first elongate member 558A or with applying a distal force to the first elongate member 558A, the anchor portion 552 may contract and/or be retracted into the lumen 540.

Reference is now made to FIGS. 6A-6G, which illustrate a method of closing a body lumen opening using a closure system 600. The example anchor member 650 of this configuration may be functionally similar to the example anchor members 150, 350, 450, and 550 previously described above and shown in FIGS. 1-5D in most respects, wherein certain features will not be described in relation to this configuration wherein those components may function in the manner as described above and are hereby incorporated into this additional configuration described below. Like structures and/or components are given like reference numerals. In addition, the closure system 600 may incorporate at least one element of the tube set 720 of FIGS. 7A-7G or closure system 800 of FIG. 8.

Figure 6A:
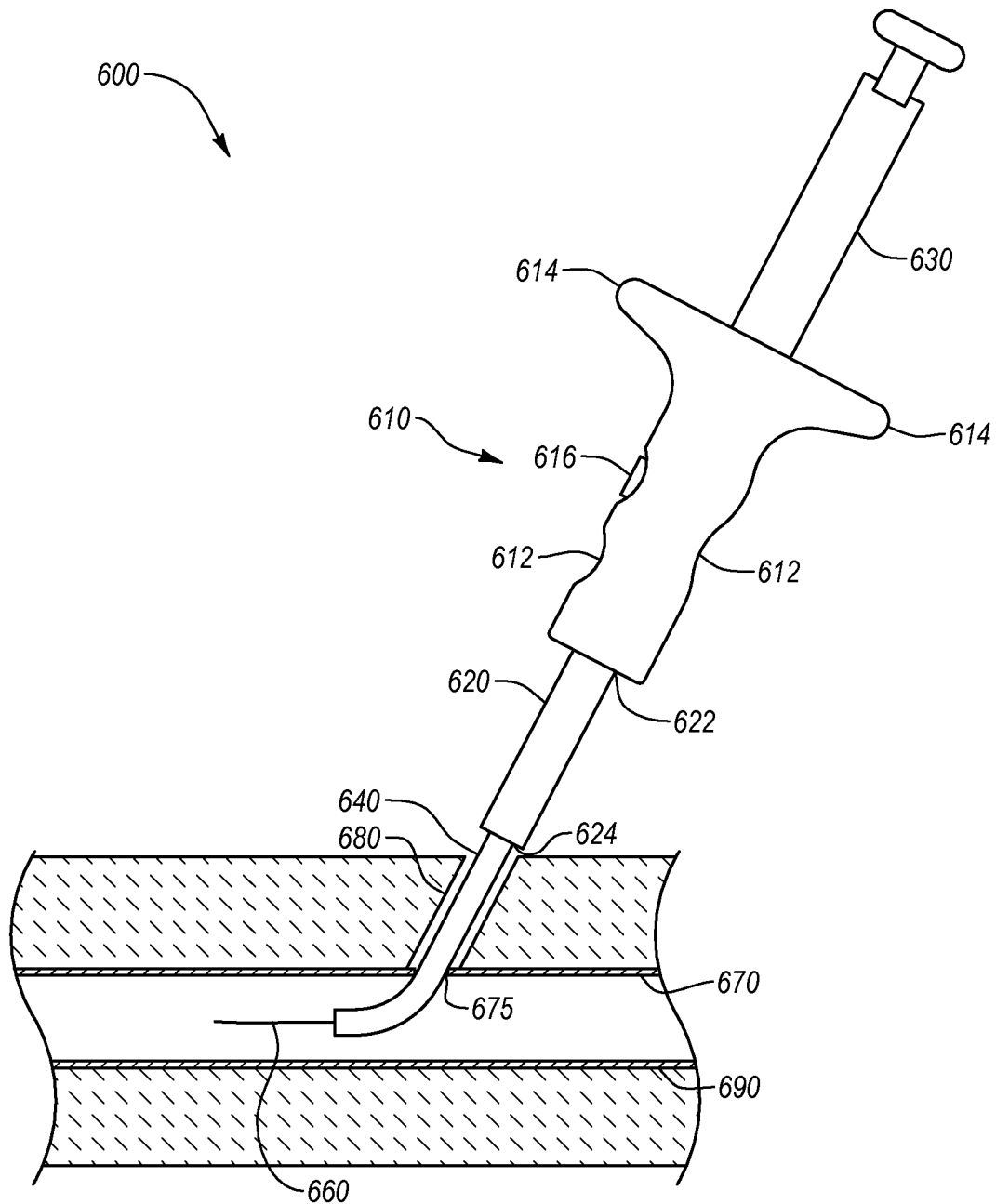
FIGS. 6A-6G disclose an example method of closing a body lumen opening in accordance with a further embodiment.

As shown in FIG. 6A, the closure system 600 may be at least partially advanced into a body lumen opening. For example, after completing a percutaneous medical procedure, an operator may advance the closure system 600 over a guidewire 660 through a tissue tract 680 and through a body lumen opening 675 in a lumen wall 670. In particular, the operator may advance the closure system 600 until the inner lumen 640 of the closure system 600 extends at least partially into the body lumen 690. Once the closure system 600 has been advanced at least partially into the body lumen 690 the operator may then retract the guidewire 660 from the body lumen 690.

Figure 6B:
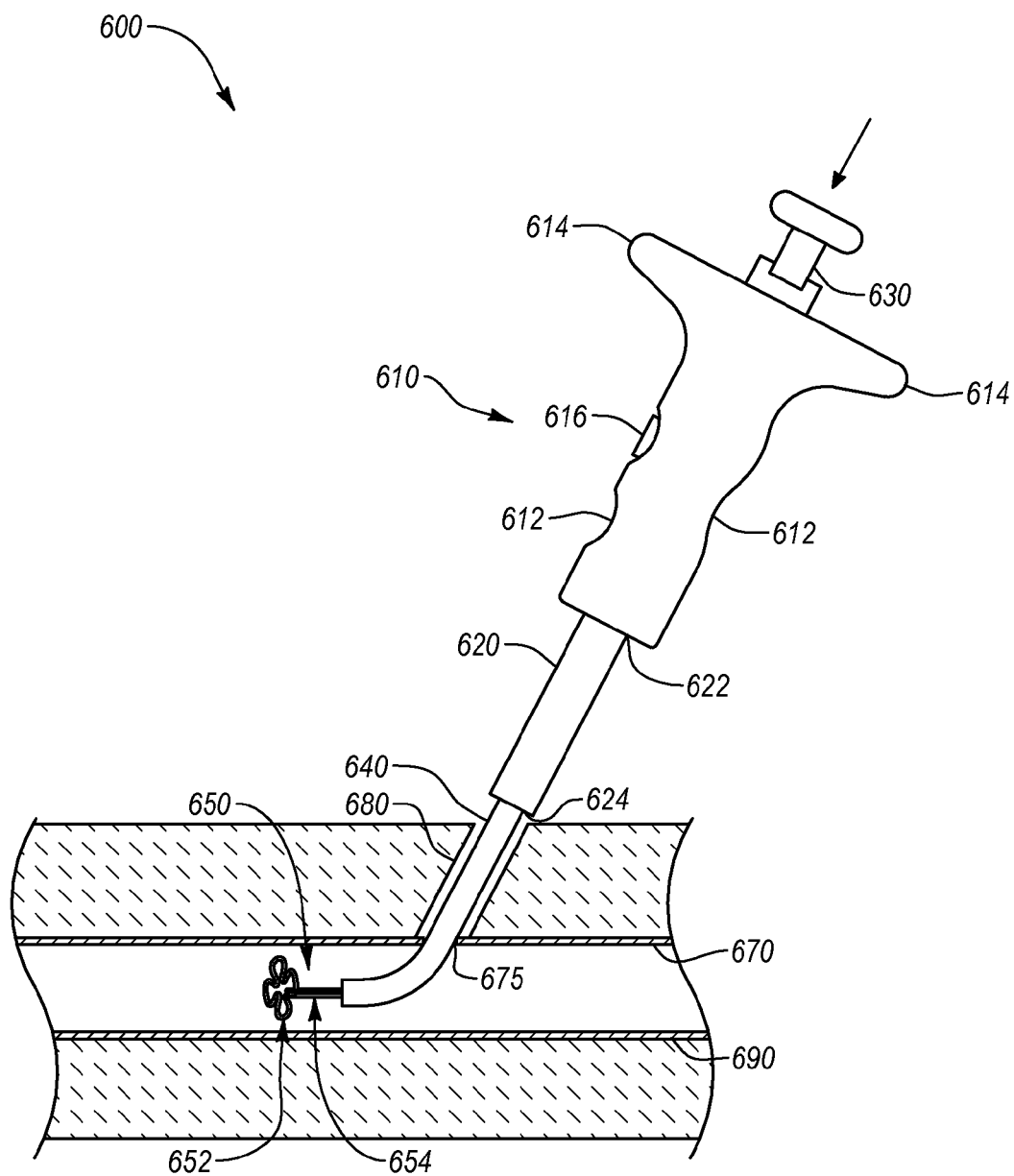
Figure 6C:
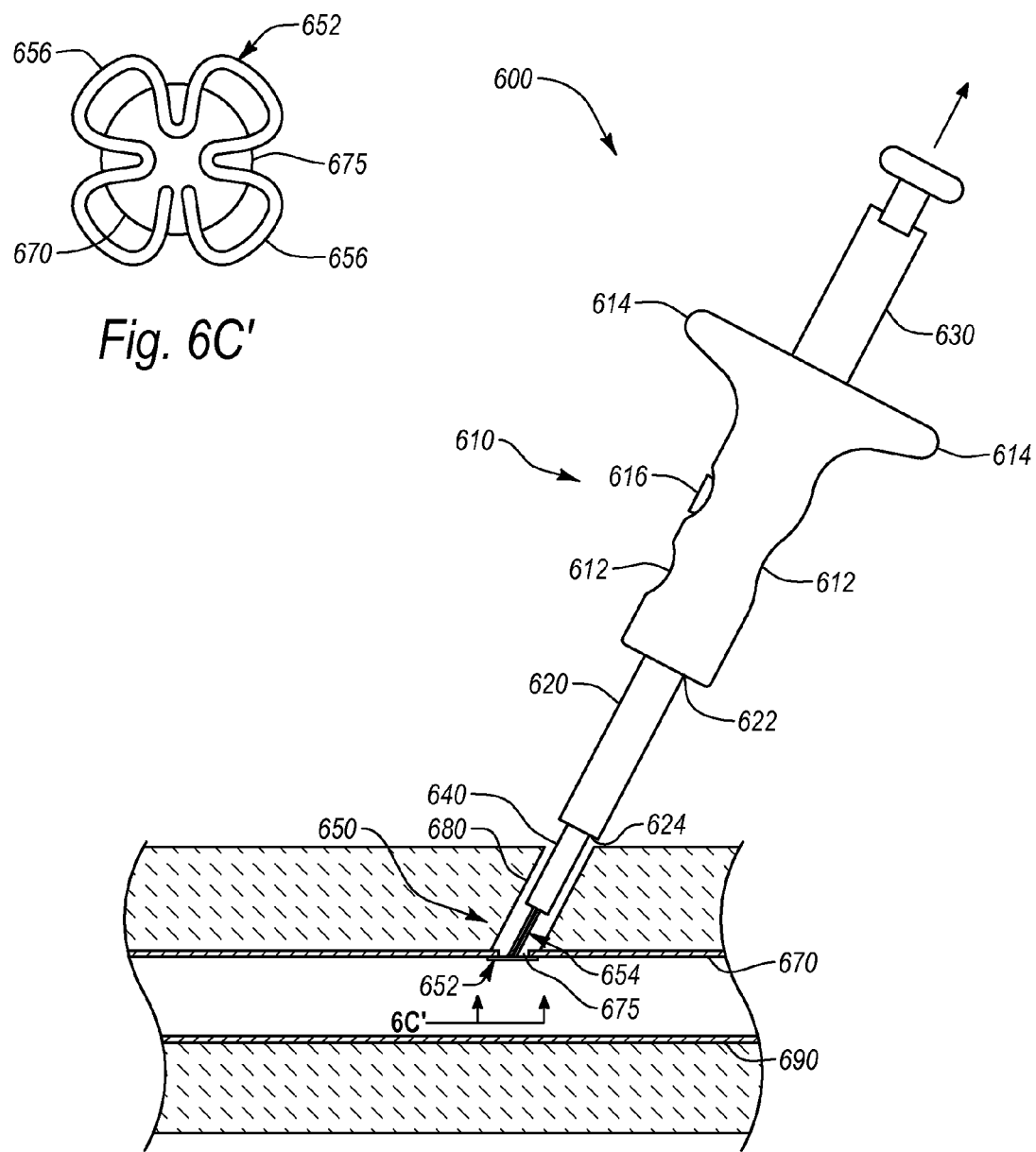
Figure 6D:
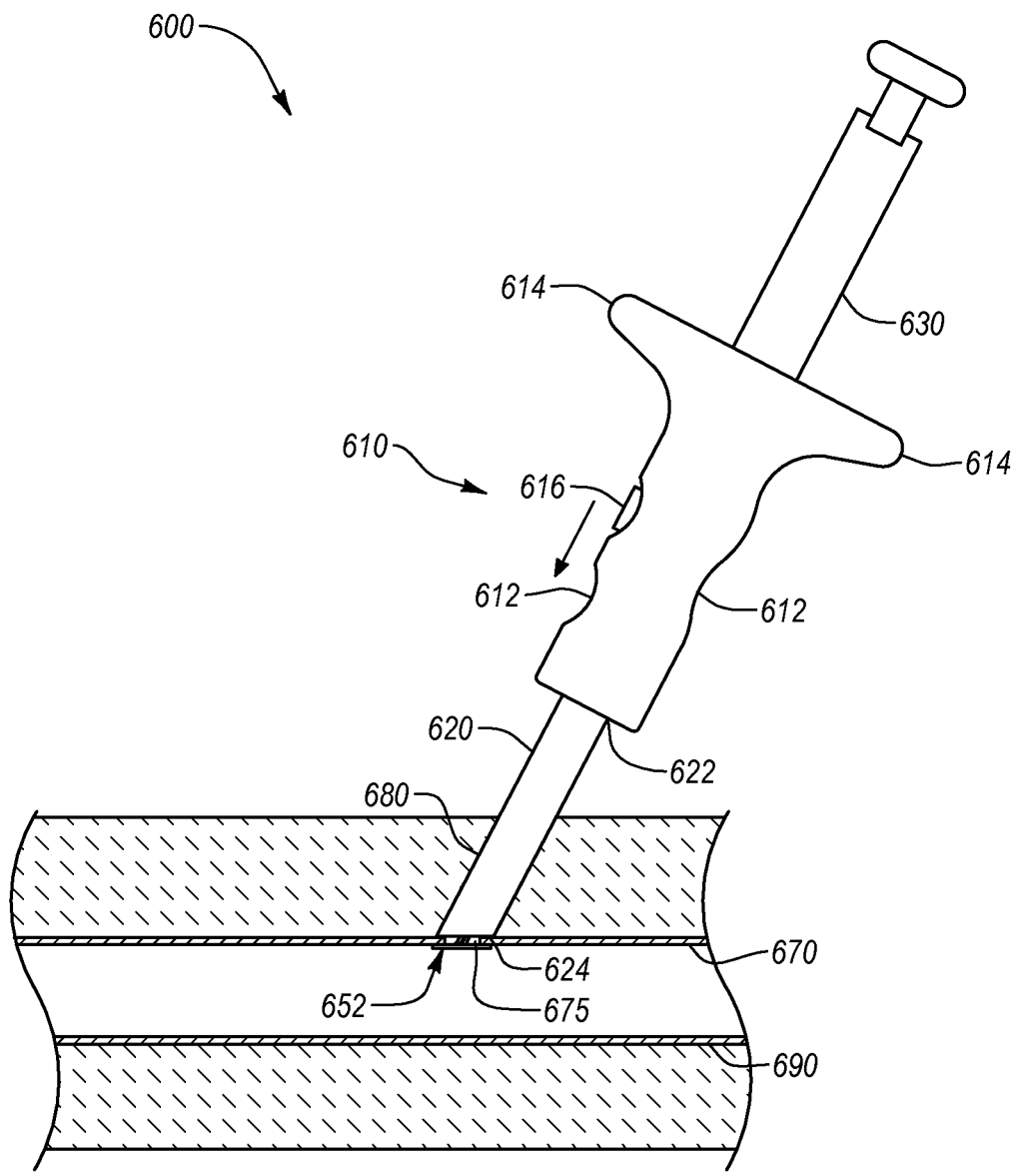

As shown in FIG. 6B, once the closure system 600 is advanced into the body lumen 690, the operator may deploy the anchor member 650 into the body lumen 690. As explained in more detail above, the operator may deploy the anchor member 650 by advancing the plunger member 630 and/or elongate portion 654 in a distal direction relative to the handle member 610, the tube set 620, and the inner lumen 640. Once deployed from the inner lumen, the anchor portion 652 of the anchor member 650 may move from an initial, contracted configuration to a deployed, expanded configuration. As shown in FIG. 6C, once the anchor portion 652 of the anchor member 650 has been deployed within the body lumen 690, the operator may retract the plunger member 630 and/or closure system 600 to position the anchor portion 652 of the anchor member 650 against the distal surface of the lumen wall 670 proximate the body lumen opening as also shown in FIG. 6C'. In particular, the operator may retract the plunger member 630 and/or closure system 600 until she feels the anchoring force or resistance from the anchor portion 652 of the anchor member 650 against the distal surface of the lumen wall 670 thereby locating the body lumen opening 675 and anchoring or securing the tissue surrounding the body lumen opening 675. As shown, the anchor portion 652 may include a plurality of projections 656 which engage and anchor the tissue of the lumen wall 670. In particular, the projections 656 may extend in a direction substantially perpendicular to the longitudinal axis of the elongate portion 654, the tube set 620, and/or inner lumen 640.

Figure 6E:
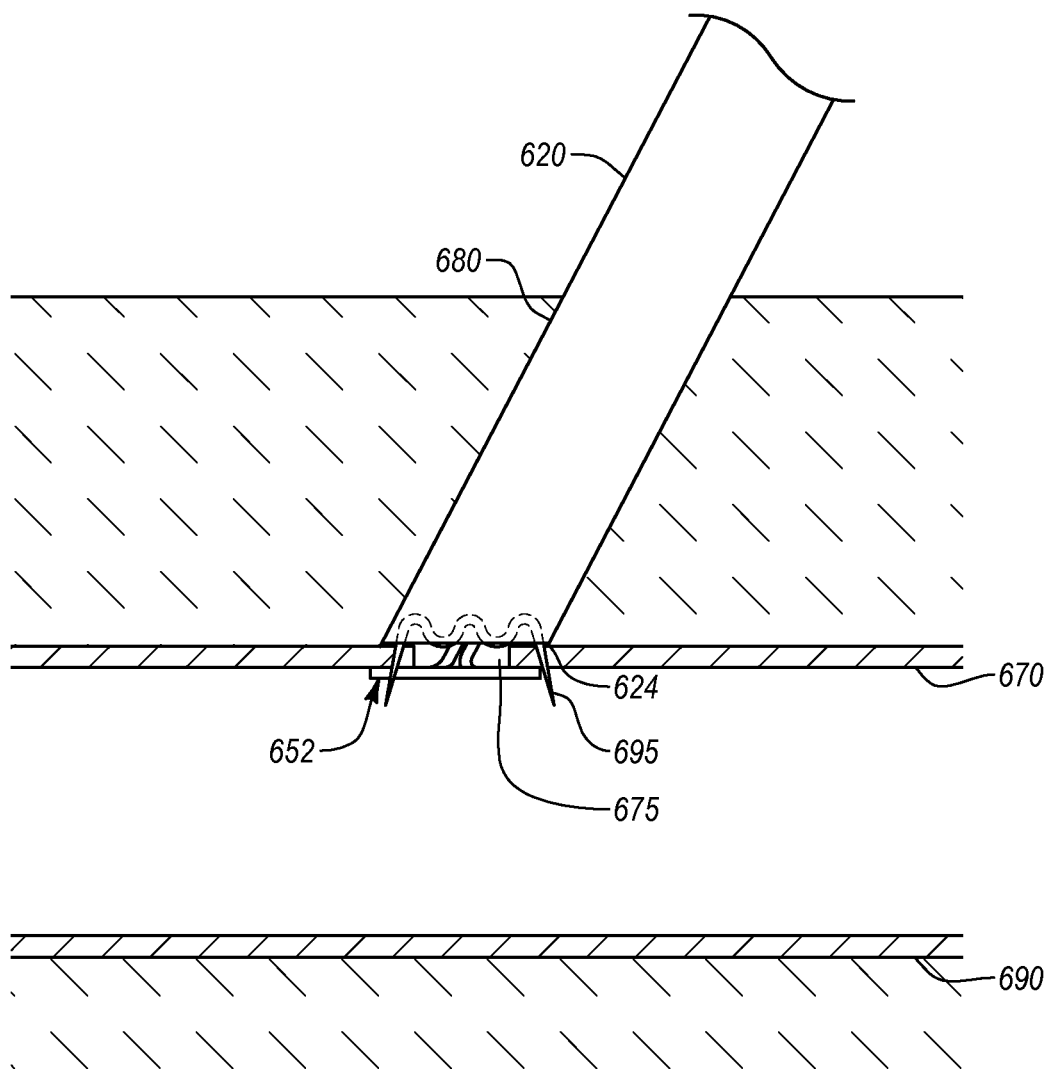

Once the anchor portion 652 has located the body lumen opening 675 and/or anchored or secured the tissue surrounding the body lumen opening 675, the operator may advance the handle member 610 in a distal direction relative to the plunger member 630 in order to advance the tube set 620 in a distal direction relative to the anchor portion 652. In particular, the operator may advance the handle member 610 and/or tube set 620 until the distal end 624 of the tube set 620 engages the proximal surface of the lumen wall 670 proximate or surrounding the lumen opening. As a result, in one embodiment, by advancing the tube set 620 in a distal direction and/or retracting the anchor portion 652 in a proximal direction, the operator may sandwich the tissue of the lumen wall 670 surrounding the body lumen opening 675 between the tube set 620 and the anchor portion 652. Accordingly, the operator may thereby engage and/or at least partially immobilize the tissue surrounding the body lumen opening 675. This may facilitate the successful deployment of a closure element 695 into the tissue surrounding the body lumen opening 675, thereby, facilitating the closure of the body lumen opening 675. In particular, the tube set 620 and the anchor portion 652 may hold the tissue in place while a closure element is deployed into the tissue. Therefore, as shown in FIG. 6E the operator may then deploy a closure element 695 into the tissue surrounding the body lumen opening. In one embodiment, the operator may depress the button 616 to eject or deploy the closure element 695 into the lumen wall 670. In particular, the closure element 695 may be deployed from an initial, open configuration to a deployed, closed configuration, thereby, engaging and bringing the tissue surrounding the body lumen opening 675 together to close the body lumen opening 675. The closure element 695 may include any device configured to close a body lumen opening 675. For example, the closure element 695 may include a staple, a clip, other similar devices, or combinations thereof.

Figure 6F:
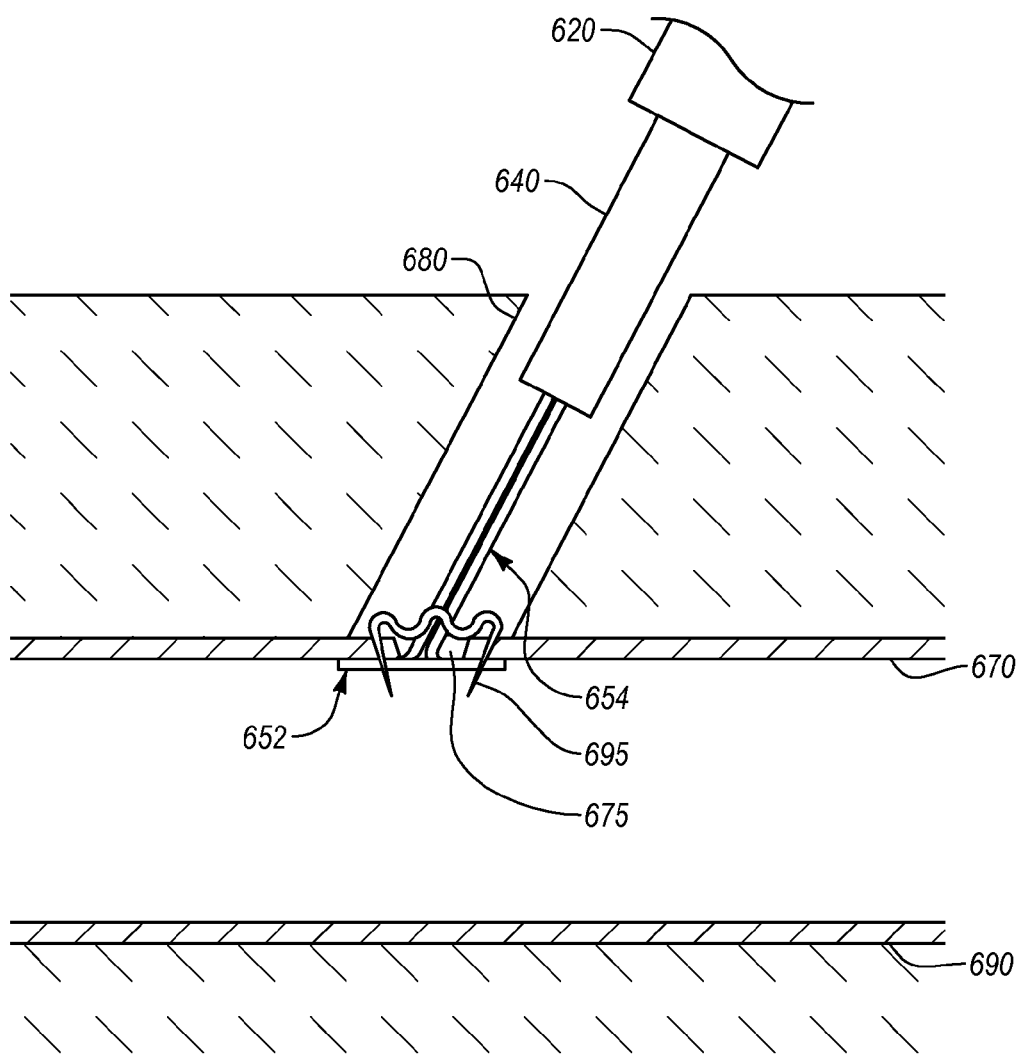
Figure 6G:
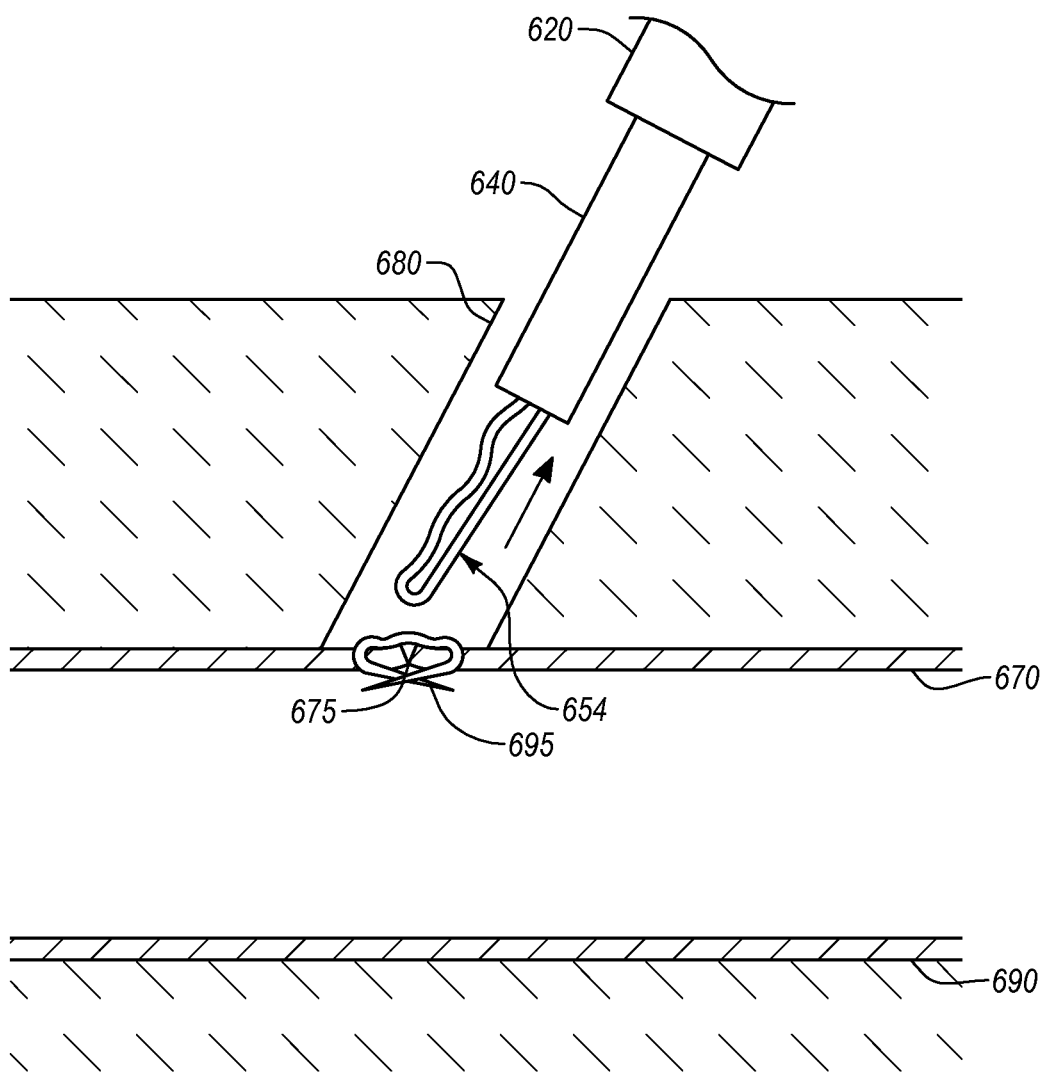

As shown in FIG. 6F, once the closure element 695 has been deployed, the handle member 610, tube set 620, and/or inner lumen 640 may be retracted out of and/or away from the body lumen 690 and tissue tract 680, as shown in FIG. 6F. Thereafter, the anchor member 650 may be retracted by retracting the elongate portion 654 in a proximal direction. For example, in one embodiment the anchor portion 652 may be pulled through the closure element 695. The closure element 695 may have superelastic properties to facilitate the withdrawal of the anchor portion 652 through the closure element 695. For example, the closure element may at least partially expand to facilitate the withdrawal of the anchor portion 652 and then return to a contracted position to close the body lumen opening 675. Accordingly, by following one or more of the acts disclosed in FIGS. 6A-6G, an operator may efficiently close a body lumen opening 675 with a greater amount of flexibility and control.

In one embodiment, the inner lumen 640 can be held in place against the outer surface of the body lumen while the anchor member 650 is retracted. Holding the inner lumen 640 may provide sufficient force to allow the anchor member and more particularly the anchor portion 652 to deform into the pre-deployment state inside of the inner lumen 640. As previously stated, this may be achieved by retracting a single elongate member. This may ensure that the closure element does not become dislodged as the anchor portion 652 is withdrawn and contracted. In further embodiments, the anchor wire may be substantially smaller than the closure element. As a result, pulling the anchor portion 652 through the closure element may not affect the positioning of the closure element since the closure element anchors in the tissue by design. In one implementation, the wire of the anchor portion 652 may be superelastic with a diameter small enough to not require substantial force to collapse the anchor portion 652 and pull it through the deployed closure element. For example, the anchor wire may have a diameter of around 0.005-0.007".

In one configuration, the anchor, closure element, and/or other aspects or components of the closure system disclosed herein can be made of a single material or of multiple materials. This can include a metal primary material and polymer/drug topcoat or a different metal top layer. The multiple layers can be resiliently flexible materials or rigid and inflexible materials, and selected combinations thereof. The use of resiliently flexible materials can provide force-absorbing characteristics, which can also be beneficial for absorbing stress and strains, which may inhibit crack formation at high stress zones. Also, the multiple layers can be useful for applying radiopaque materials. For example, types of materials that are used to make a closure element can be selected so that the closure element is capable of being in a first orientation (e.g., delivery orientation) during placement and capable of transforming to a second orientation (e.g., deploying orientation) when deployed to close the opening in a lumen.

Embodiments of the anchor, closure element and the like can include a material made from any of a variety of known suitable biocompatible materials, such as a biocompatible shape memory material (SMM). For example, the SMM can be shaped in a manner that allows for a delivery orientation while within the tube set, but can automatically retain the memory shape of the closure element once deployed into the tissue to close the opening. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have an initial shape that can then be configured into a memory shape by heating the SMA and conforming the SMA into the desired memory shape. After the SMA is cooled, the desired memory shape can be retained. This allows for the SMA to be bent, straightened, twisted, compacted, and placed into various contortions by the application of requisite forces; however, after the forces are released, the SMA can be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture. This can be used to tune the closure element so that it reverts to the memory shape to close the arteriotomy when deployed at body temperature and when being released from the tube set.

For example, the primary material of a closure element can be of a NiTi alloy that forms superelastic nitinol. In the present case, nitinol materials can be trained to remember a certain shape, retained within the tube set, and then deployed from the tube set so that the tines penetrate the tissue as it returns to its trained shape and closes the opening. Also, additional materials can be added to the nitinol depending on the desired characteristic. The alloy may be utilized having linear elastic properties or non-linear elastic properties.

An SMP is a shape-shifting plastic that can be fashioned into a closure element in accordance with the present disclosure. Also, it can be beneficial to include at least one layer of an SMA and at least one layer of an SMP to form a multilayered body; however, any appropriate combination of materials can be used to form a multilayered device. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of an endoprosthesis by heating it above the Ttr, fixing the SMP into the new shape, and cooling the material below Ttr. The SMP can then be arranged into a temporary shape by force and then resume the memory shape once the force has been released. Examples of SMPs include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present disclosure.

An anchor, closure element and the like may have at least one layer made of an SMM or suitable superelastic material and other suitable layers can be compressed or restrained in its delivery configuration within the garage tube or inner lumen, and then deployed into the tissue so that it transforms to the trained shape. For example, a closure element transitions to close the opening in the body lumen while an anchor may expand to anchor the closure system.

Also, the anchor, closure element, or other aspects or components of the closure system can be comprised of a variety of known suitable deformable materials, including stainless steel, silver, platinum, tantalum, palladium, nickel, titanium, nitinol, nitinol having tertiary materials (U.S. 2005/0038500, which is incorporated herein by reference, in its entirety), niobium-tantalum alloy optionally doped with a tertiary material (U.S. 2004/0158309, 2007/0276488, and 2008/0312740, which are each incorporated herein by reference, in their entireties) cobalt-chromium alloys, or other known biocompatible materials. Such biocompatible materials can include a suitable biocompatible polymer in addition to or in place of a suitable metal. The polymeric closure element can include biodegradable or bioabsorbable materials, which can be either plastically deformable or capable of being set in the deployed configuration.

In one embodiment, the closure element or anchor may be made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol closure element. The nitinol closure element has improved radiopacity yet retains its superelastic and shape memory behavior and further maintains a thin body thickness for high flexibility.

In one embodiment, the anchor or closure element can be made at least in part of a high strength, low modulus metal alloy comprising Niobium, Tantalum, and at least one element selected from the group consisting of Zirconium, Tungsten, and Molybdenum.

In further embodiments, the closure element or anchor can be made from or be coated with a biocompatible polymer. Examples of such biocompatible polymeric materials can include hydrophilic polymer, hydrophobic polymer biodegradable polymers, bioabsorbable polymers, and monomers thereof. Examples of such polymers can include nylons, poly (alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

Reference is now made to FIGS. 7A-7G, which disclose an example tube set 720. The example tube set 720 of this configuration may be functionally similar to the example tube set 120 and 620 previously described above and shown in FIGS. 1, 2, and 6A-6G in most respects, wherein certain features will not be described in relation to this configuration wherein those components may function in the manner as described above and are hereby incorporated into this additional configuration described below. Like structures and/or components are given like reference numerals. Additionally, the tube set 720 may incorporate at least one component of the tube set 820 of FIG. 8. In further embodiments, the tube set 720 may be utilized with the closure systems 100 and 600 disclosed in FIGS. 1, 2A-2D, and 6A-6G.

The tube set 720 may include a garage sheath 722, a pusher tube 724, and a carrier tube 726. In addition, the tube set 720 may be configured to receive or house a locator element and closure element 795. In one embodiment, the tube set 720 may house an inner lumen 740, and/or anchor member 750. In further embodiments, the tube set 720 may be configured to deliver and/or deploy the closure element 795 in order to close an opening in a lumen wall.

The garage sheath 722 may be configured to cover, protect, and/or house the closure element 795 within the tube set 720 and/or other components of the tube set 720. In one embodiment, the garage sheath 722 may be generally tubular in shape. In a further embodiment, the distal end of the garage sheath 722 may have a different configuration than the remainder of the garage sheath 722. For example, the distal end of the garage sheath 722 may have an inwardly tapered configuration. In further embodiments, the distal end may be configured to at least partially expand to facilitate deployment of the closure element 795. For example, the distal end of the garage sheath 722 may include one or more longitudinal slits thereby forming one or more flanges that may deflect radially outwardly in order to facilitate deployment of the closure element 795.

In addition to the garage sheath 722, the tube set 720 may include a pusher tube 724. The pusher tube 724 may be configured to deploy the closure element 795. In one embodiment, the pusher tube 724 may be generally tubular in shape along the length thereof. The pusher tube 724 may be disposed between the carrier tube 726 and the garage sheath 722 and proximal of the closure element 795. In a further embodiment, the distal end of the pusher tube 724 may include one or more fingers or projections extending from the distal end of the pusher tube 724 and configured to help stabilize and/or deploy the closure element 795. For example, the fingers or projections extending from the distal end of the pusher tube 724 may be configured in size to fit into corresponding waves, undulations, or other features along a proximal edge or surface of the closure element 795.

In addition to the pusher tube 724, the tube set 720 may include a carrier tube 726. The carrier tube 726 may be configured to carry the closure element 795 in a delivery configuration to a location proximate an opening in a body lumen. In one embodiment, the carrier tube 726 may be generally tubular in shape along the length thereof. The carrier tube 726 may be disposed at least partially within the pusher tube 724 with the closure element 795 disposed thereon. In further embodiments, the distal end of the carrier tube 726 may have a different configuration than the remainder of the carrier tube 726. For example, the distal end of the carrier tube 726 may flare radially outwards to facilitate successful deployment of the closure element 795. For example, the flared distal end of the carrier tube 726 may direct one or more elements of the closure element 795 outwards to engage tissue surrounding the opening in the body lumen to better close the body lumen opening.

The garage sheath 722, pusher tube 724, and/or carrier tube 726 may include any of a number of materials, such as biocompatible polymers and/or metals. In one example, one or more of the garage sheath 722, pusher tube 724, and/or carrier tube 726 may include stainless steel. The materials of the garage sheath 722, pusher tube 724, and/or carrier tube 726 may have rigid, semi-rigid, or flexible mechanical properties as desired for a particular embodiment.

Figure 7A:
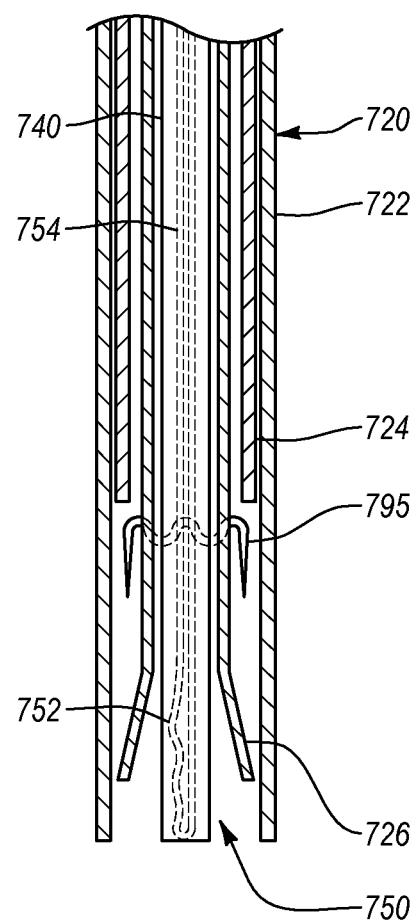
FIGS. 7A-7G disclose the operation of an example tube set.

The garage sheath 722, pusher tube 724, and/or carrier tube 726 may be longitudinally movable relative to each other. The independent longitudinal movement of each element of the tube set 720 may facilitate the deployment of the closure element 795 and corresponding closure of a body lumen opening. As shown in FIG. 7A, the tube set 720 may have an initial delivery configuration, in which the closure element 795 is disposed on the corner tube 726 and the anchor member 750 is disposed within the carrier tube 726. In this initial delivery configuration, a medical care provider or user can move the tube set 720 into position within or near an opening in a body lumen.

Figure 7B:
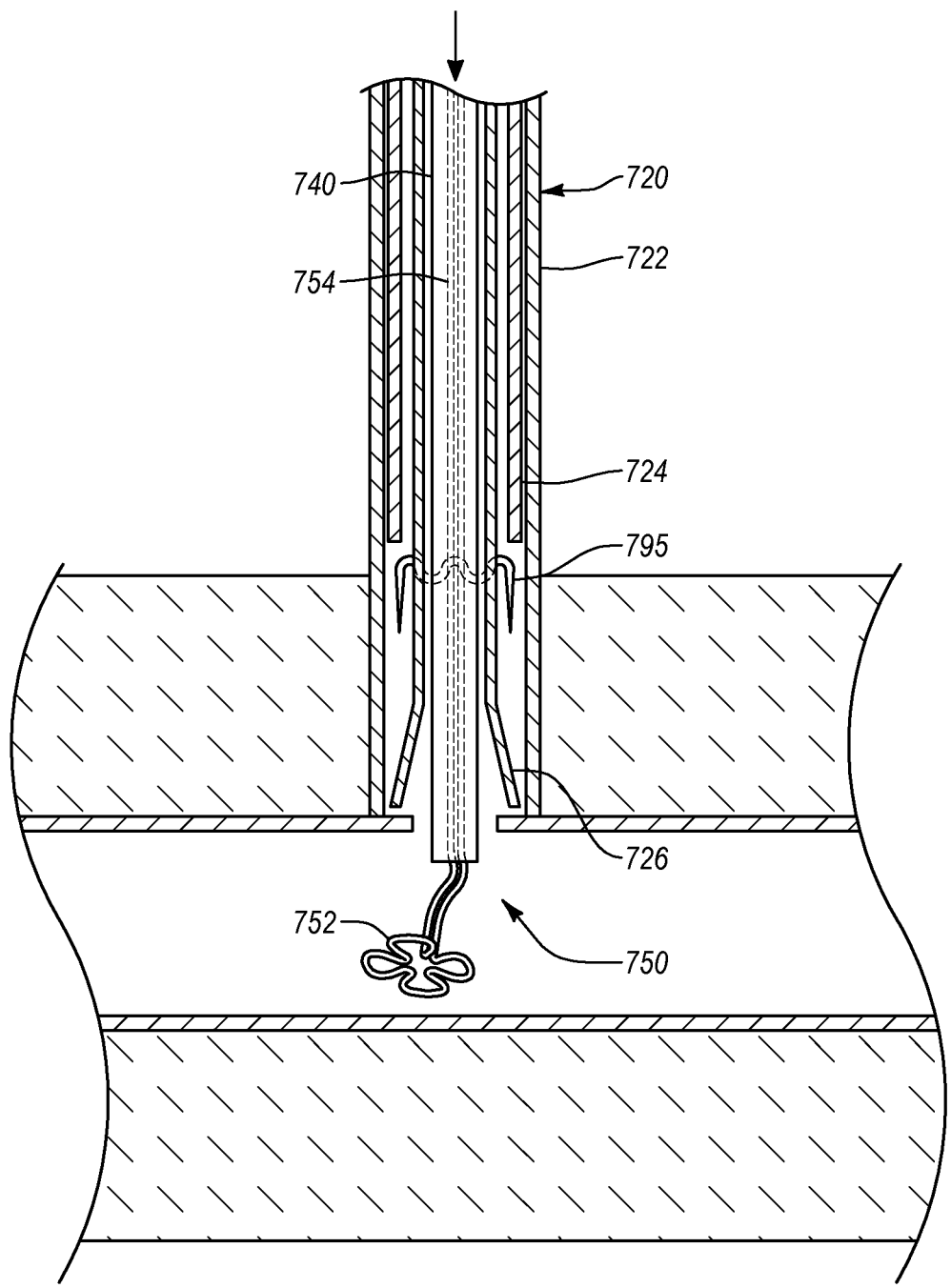

Once the tube set 720 is in position proximate a body lumen opening, the user of the tube set 720 can advance the inner lumen 740 at least partially into the body lumen, as shown in FIG. 7B. Once the inner lumen 740 is partially disposed within the body lumen, the user may advance the anchor portion 752 of the anchor 750 by advancing the elongate member(s) 754 relative to the inner lumen 740 and tube set 720. As a result, the anchor portion 752 may deploy from a delivery configuration to a deployed configuration as described in more detail above.

Figure 7C:
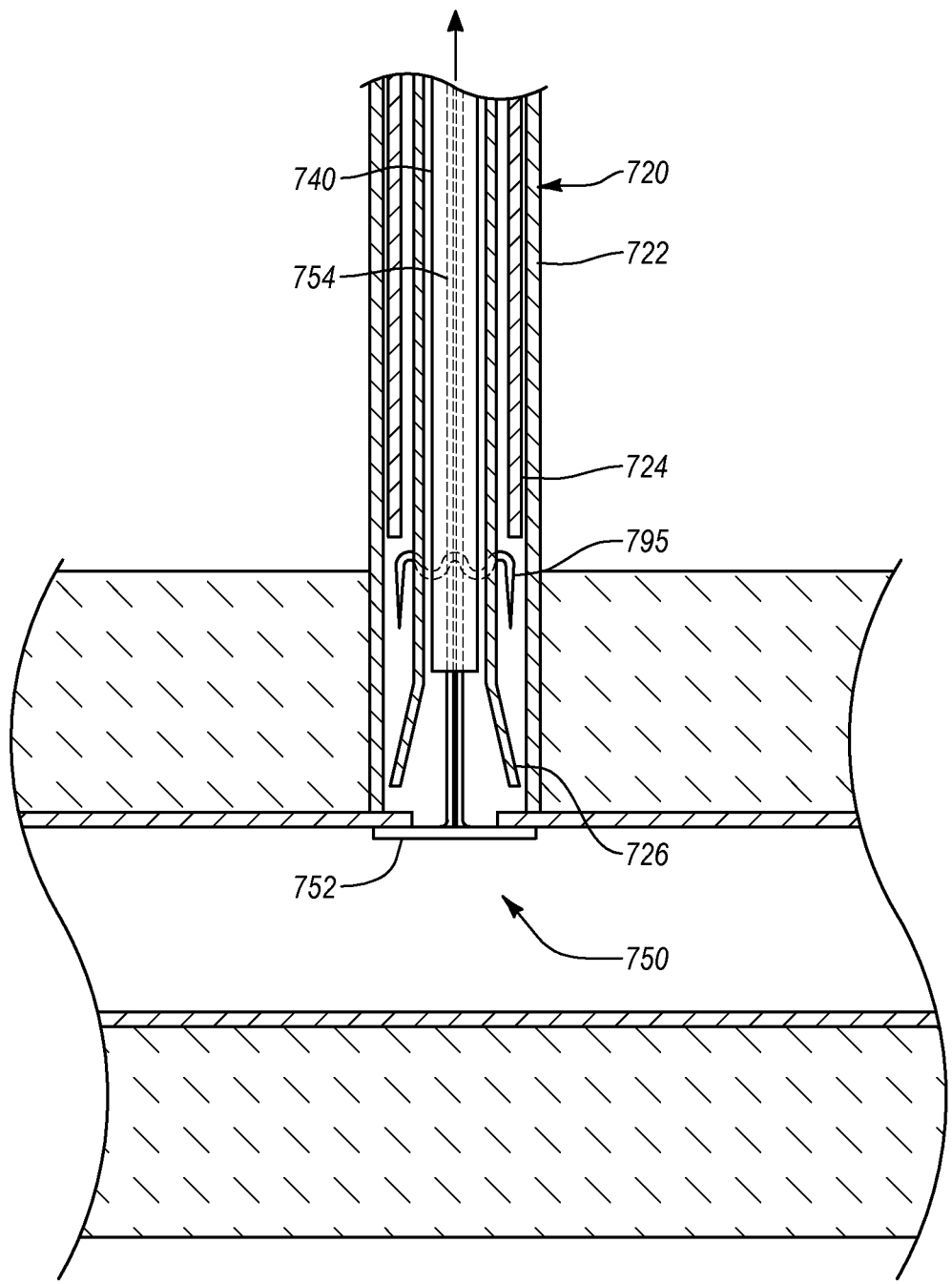
Figure 7D:
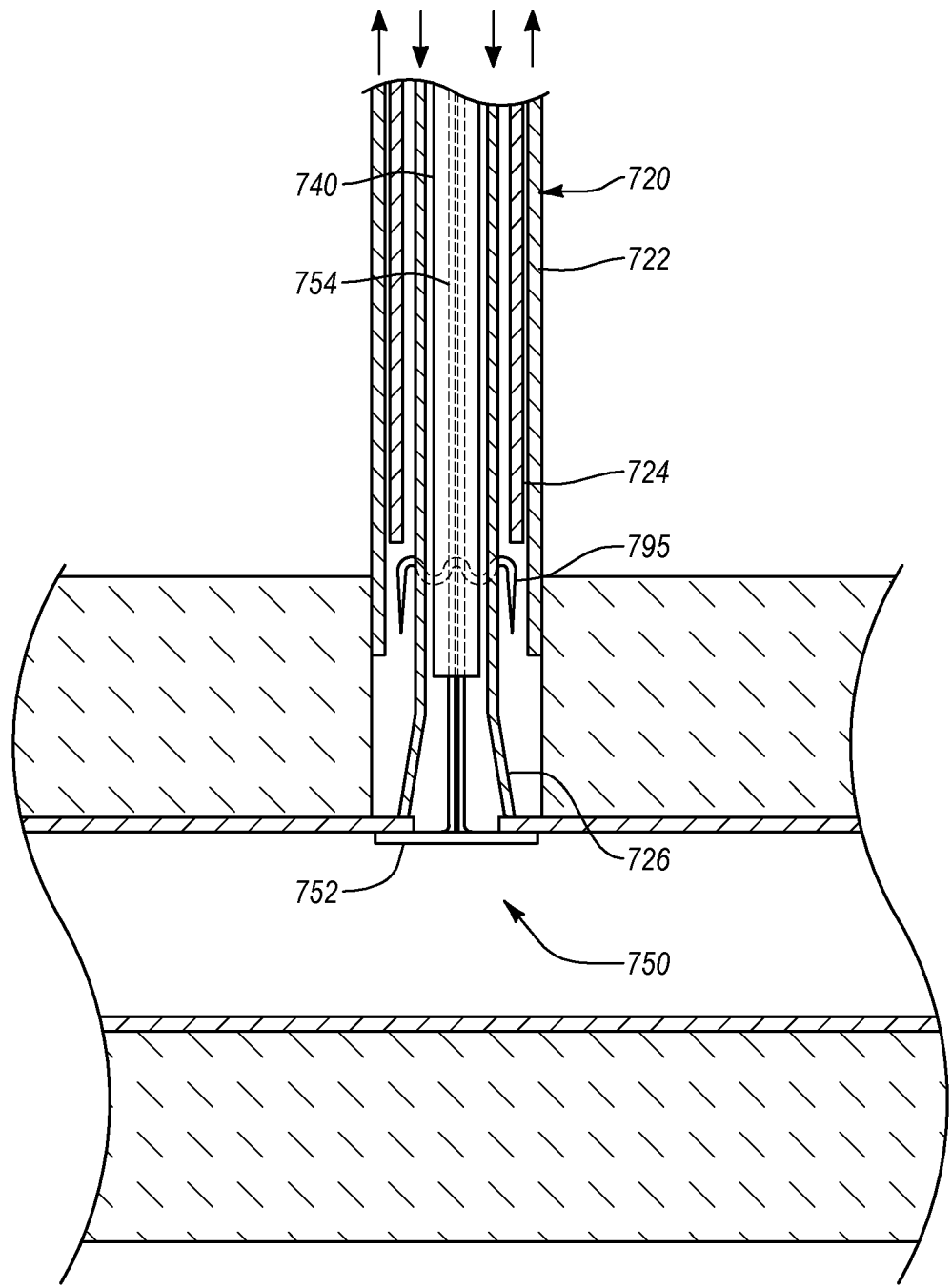

Once the anchor portion 752 is deployed within the body lumen, the user may retract the anchor 750 in a proximal direction to position the anchor portion 752 against the distal surface of the body lumen surrounding the opening, as shown in FIG. 7C. In a further embodiment, the user can retract the garage tube 722 in order to expose the closure element 795, as shown in FIG. 7D.

Figure 7E:
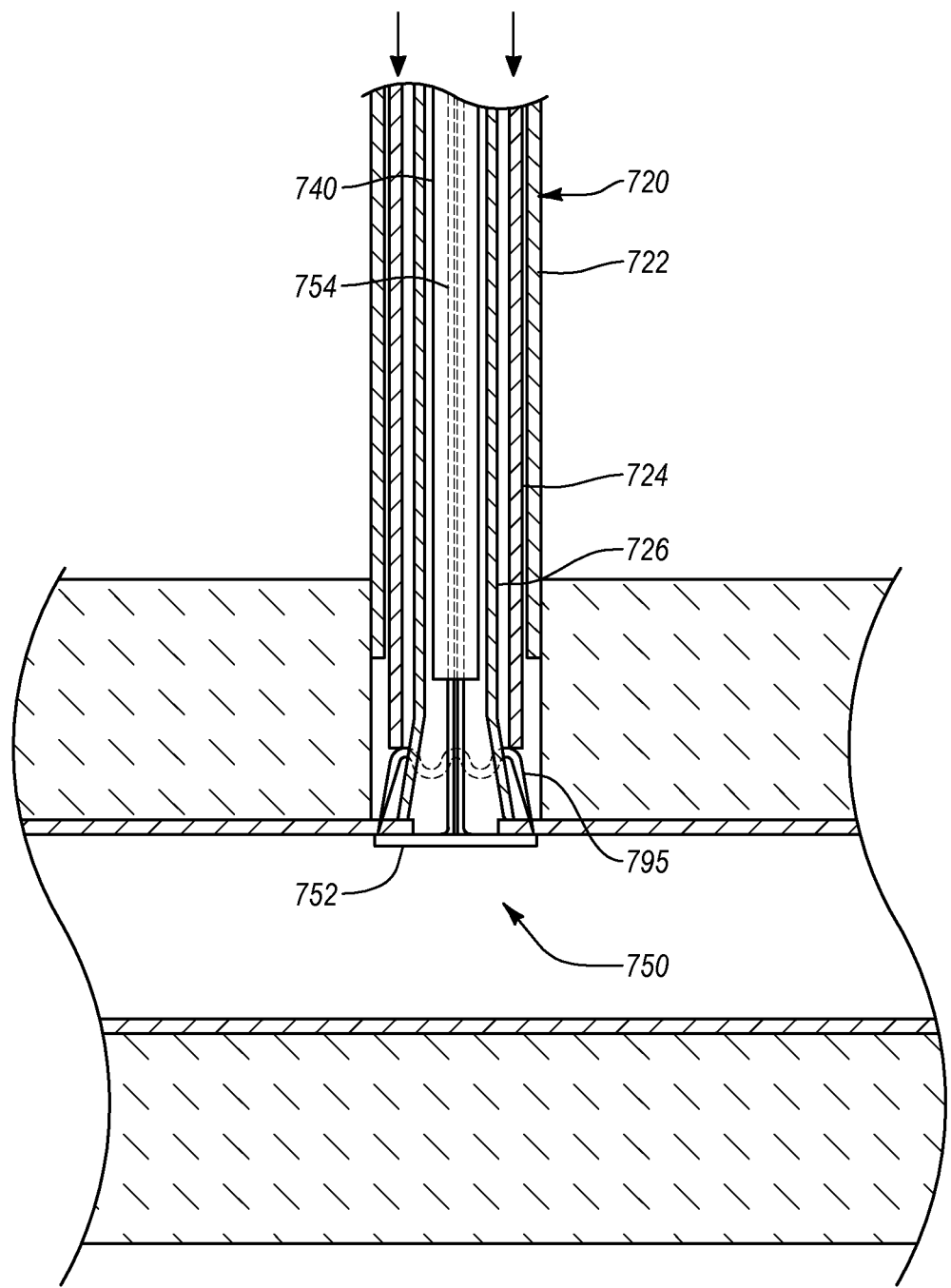

Once the carrier tube 726 is anchored against the body lumen, the user can deploy the closure element 795 by advancing the pusher tube 724 in a distal direction relative to the carrier tube 726, as shown in FIG. 7E. As the pusher tube 724 advances, it may come into contact with the closure element 795 and begin to advance the closure element 795 in a distal direction relative to the carrier tube 726. In further embodiments, as the closure element 795 advances, the flared distal end of the carrier tube 726 may expand the closure element 795 and direct one or more tines of the closure element 795 radially outward to better engage the tissue surrounding the opening in the body lumen.

Figure 7F:
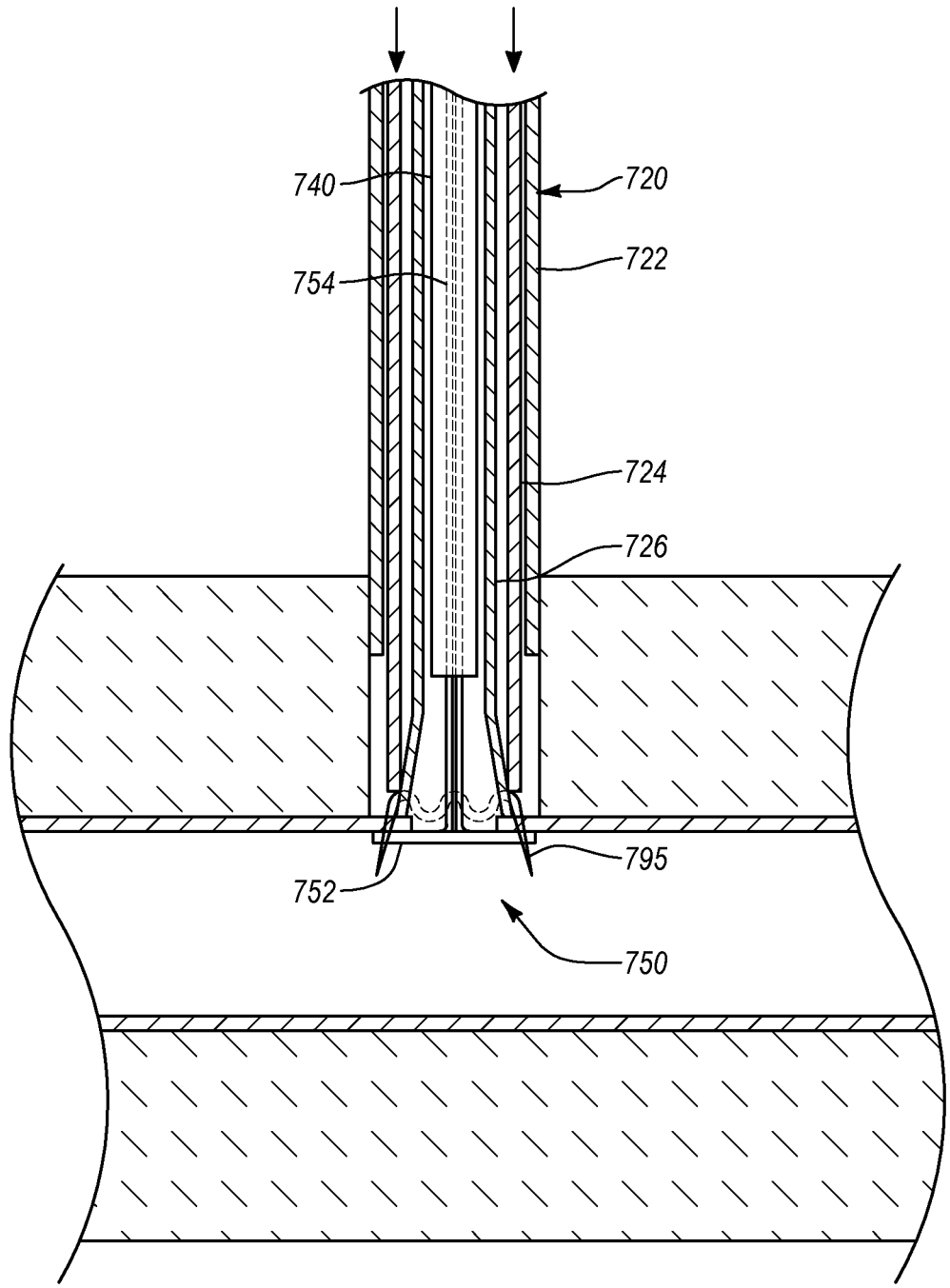
Figure 7G:
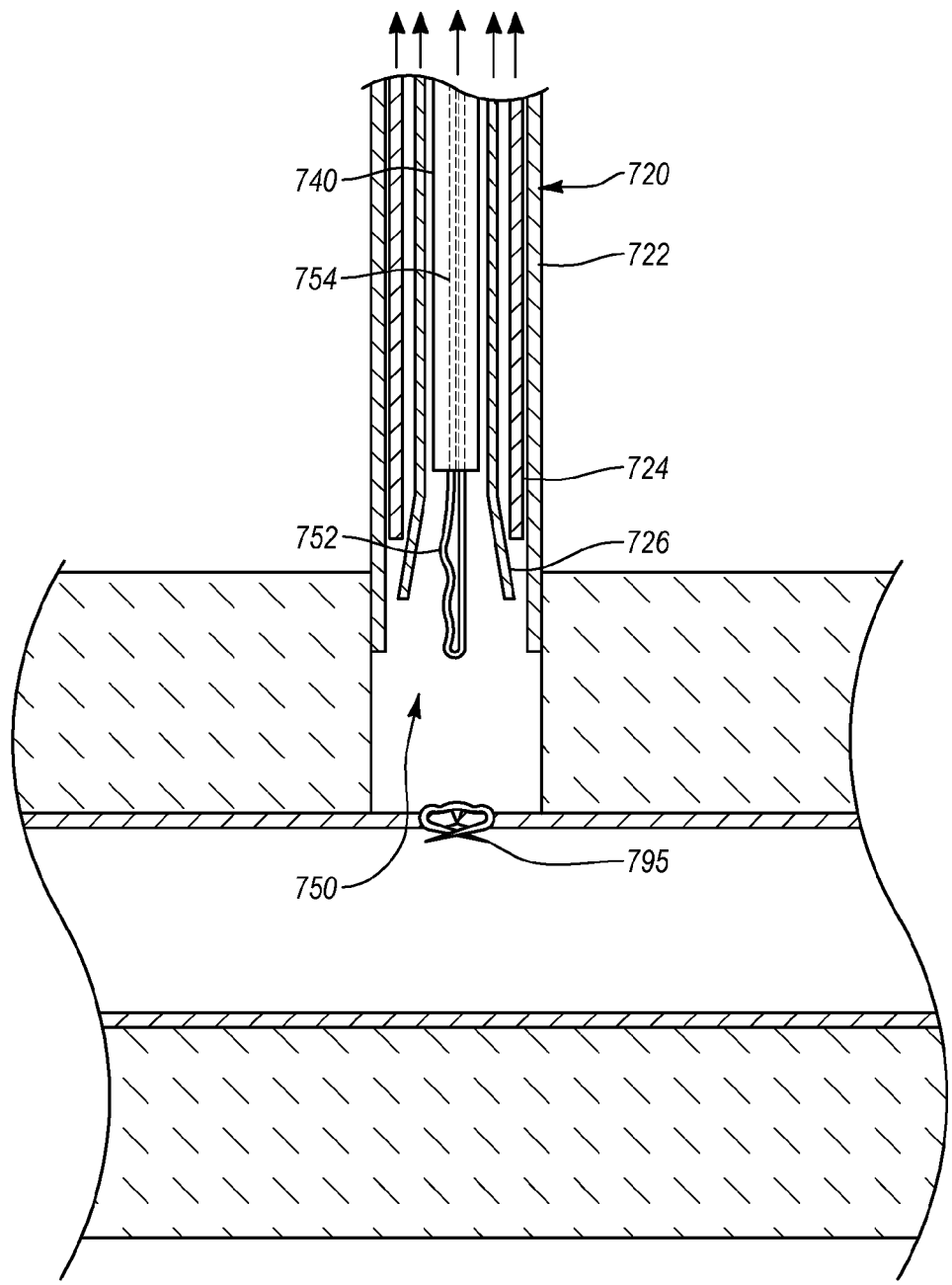

As shown in FIG. 7F, the user can continue to advance the pusher tube 724 until the closure element 795 extends at least partially beyond the distal end of the carrier tube 726 and into engagement with the body lumen. Once deployed beyond the carrier tube 726, the closure element 795 may move from its expanded, delivery configuration to a deployed, collapsed configuration, thereby closing the body lumen opening, as shown in FIG. 7G. In addition, the user can retract the anchor portion 752 through the deployed closure element 795, as disclosed in more detail above. In further embodiments, the user may retract the tube set 720 and anchor 750 in a proximal direction away from the body lumen and out of the tissue tract, thereby leaving the deployed closure element in place.

Figure 8:
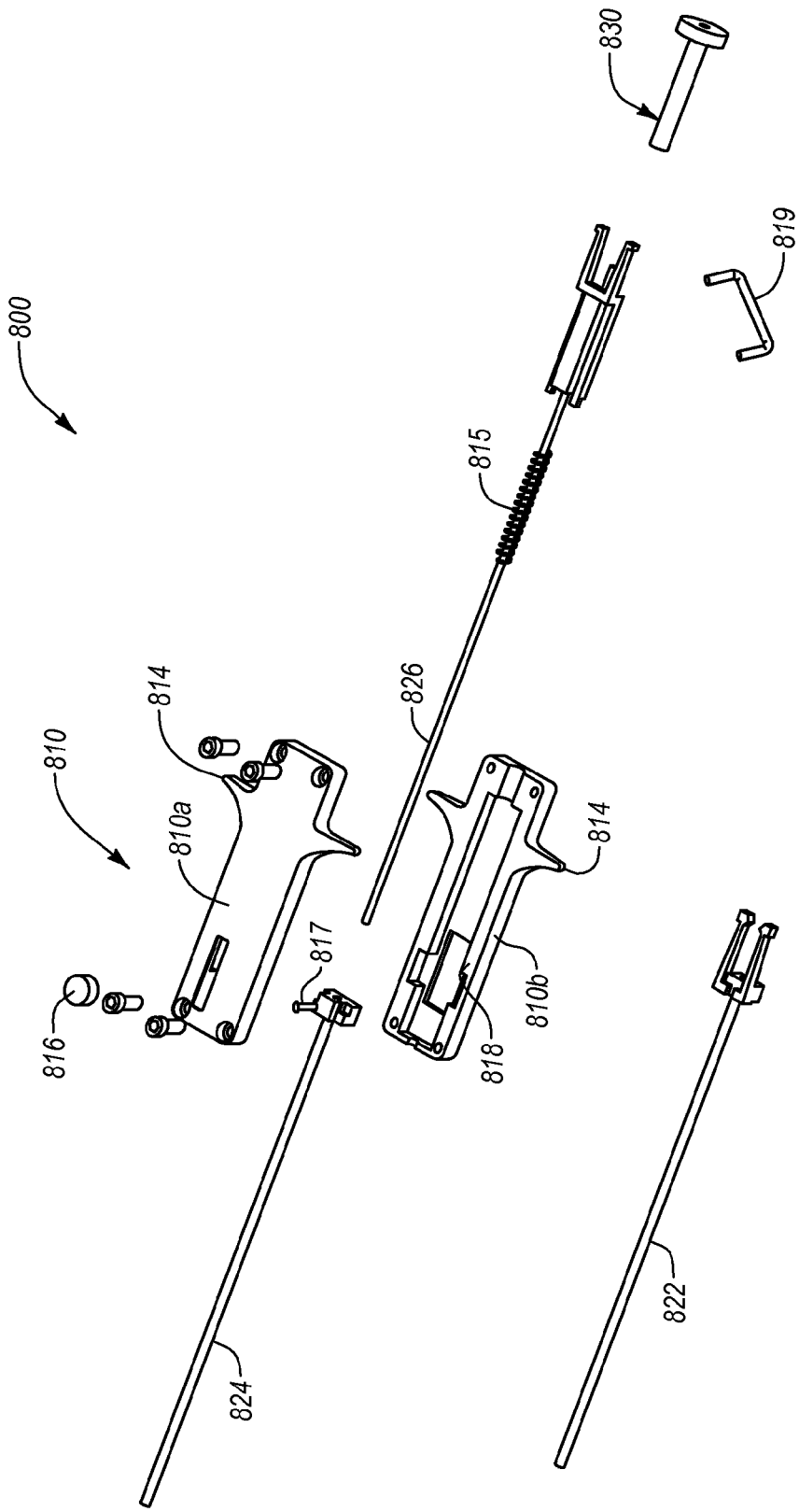
FIG. 8 discloses an exploded view of an additional example closure system in accordance with a further embodiment.

Reference is now made to FIG. 8, which illustrates an additional example closure system 800 in accordance with a further embodiment of the present disclosure. The example closure system 800 of this configuration may be functionally similar to the example closure systems 100 and 600 and tube set 720 previously described above and shown in FIGS. 1, 2A-2D, 6A-6G, and 7 in most respects, wherein certain features will not be described in relation to this configuration wherein those components may function in the manner as described above and are hereby incorporated into this additional configuration described below. Like structures and/or components are given like reference numerals. Additionally, the closure systems 100 and 600 and tube set 720 may incorporate one or more components of the closure system 800.

As shown, the closure system 800 may include a handle member 810, a tube set 820 configured to couple with or be partially disposed within the handle member 810, and a plunger member 830 and firing pin 816 configured for manipulation by a user in order to operate the closure system 800 and deploy a closure element, such as a clip or staple. As a result, a user, such as a physician, may utilize the closure system 800 and the elements thereof to close an opening in a body lumen.

The handle member 810 of the closure system 800 may be configured to assist an operator, such as a physician, to grip, manipulate, advance, and/or operate the closure system 800 in order to close a body lumen opening. In one embodiment, the handle member may have an upper portion 810*a* and a lower portion 810*b*. The upper portion 810*a* and lower portion 810*b* may be connected using one or more fasteners, adhesives, welds, and/or other mechanisms. In further embodiments, the handle member may define a recess 818 configured to house one or more components of the closure system 800. The recess 818 may be configured to receive components of the tube set 820 as well as other components of the closure system 800 disclosed in FIG. 8 and described in more detail below. In yet further embodiments, the recess 818 may have openings along the sides thereof configured to receive portions of the tube set 820 during operation of the closure system 800.

As shown, the closure element 800 may also include a tube set 820. In one embodiment, the tube set 820 may include a garage tube 822, pusher tube 824, and carrier tube 826. In further embodiments, each of the garage tube 822, pusher tube 824, and carrier tube 826 may include a slider block at its proximal end configured to be disposed within and slide along the recess 818 of the handle member 810. Each of the slider blocks may be further configured to lock within the openings along the sides of the recess 818 to restrict or control the movement of each member of the tube set 820. For example, after moving in a distal direction to position the components of the tube set 820 for deployment of a closure element, one or more of the slider blocks may lock into the openings to restrict further movement, such as in a proximal direction.

The handle member 810 may also be operatively associated with any number of mechanisms configured to deploy a closure element. For example, the handle member 810 may include a button 816 operatively associated with one or more mechanisms configured to deploy a closure element. The button 816 may be operatively associated with a firing pin 817 configured to release stored energy to fire or deploy a closure element. For example, the closure system 800 may store energy in a spring 815. In one embodiment, the spring 815 may be disposed on and/or between components of the tube set 820. In further embodiments, the energy may be transferred to the spring 815 by depressing the plunger member 830. A user may release the stored energy by depressing the button 816, which may release the firing pin 817. In one embodiment, the stored energy may transfer to the pusher tube 824 in order to deploy the closure element. As a result, an operator may depress the button 816 in order to push, fire, or eject a closure element from the tube set 820 into the tissue of a body lumen to close a body lumen opening.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:
1. A closure system comprising:
   a handle member;
   a tube set configured to deliver or deploy a closure element, the tube set having a distal end and a proximal end, the proximal end of the tube set being coupled to the handle member;
   an inner lumen disposed at least partially within the tube set;
   a plunger member movably coupled to the handle member; and
   an anchor member at least partially disposed within the inner lumen, the anchor member comprising an anchor portion, a first elongate portion, and a second elongate portion, the anchor portion being disposed in the inner lumen in an initial configuration and configured to move to an expanded configuration in a transverse plane to said elongate portion once deployed from the inner lumen without additional external force, the expanded configuration including a first portion and a second portion, the second portion being an inverted mirror image of the first portion about an intersection between the first portion and the second portion, the first elongate portion, the second elongate portion, the first portion, and the inverted second portion are continuously connected the anchor member configured to locate the closure system within a body lumen, the anchor member being configured to be retracted through the closure element.

2. The closure system of claim 1, the plunger member being longitudinally slidable with respect to the handle member.

3. The closure system of claim 1, the closure element disposed within the tube set in an initial configuration and being configured to move to a deployed configuration once deployed from the tube set.

4. The closure system of claim 1, the plunger member being at least partially disposed within a recess in the handle member.

5. The closure system of claim 1, the inner lumen being movable relative to the tube set and handle member.

6. The closure system of claim 1, the anchor member comprising shape memory or superelastic materials.

7. The closure system of claim 6, the anchor portion further comprising an elongate wire forming the elongate portion and the anchor portion.

8. The closure system of claim 6, wherein the first or second elongate portion of the anchor member is coupled to the plunger member.

9. The closure system of claim 8, wherein the plunger member is configured to slide in a distal direction relative to the handle member to deploy and expand the anchor portion of the anchor member from the initial configuration to the expanded configuration.

10. The closure system of claim 9, wherein the handle member is configured to move in a distal direction relative to the plunger member to advance the distal end of the tube set to proximity with the anchor portion of the anchor member.

11. The closure system of claim 1, the expanded configuration of the anchor portion comprising a plurality of projections laying in a plane that is transverse to a longitudinal axis of the elongate portion of the anchor member.

12. The closure system of claim 11, wherein at least one of the projections is shaped similar to a petal or leaf.

13. The closure system of claim 12, wherein the expanded configuration of the anchor portion is substantially similar in shape to a four-leaf clover, figure eight, a ball, or a configuration having more than four leaves.

14. The closure system of claim 1, further comprising the handle member or tube set being configured to deploy the closure element from the distal end of the tube set.

15. The closure system of claim 1, the closure element comprising a clip or staple.

16. The closure system of claim 1, the handle member further comprising one or more indentations or flanges configured to facilitate gripping or manipulating the handle member.

17. The closure system of claim 1, wherein the tube set comprises a garage tube, a pusher tube, and a carrier tube.

18. A closure system comprising:
a handle member;
a tube set including one or more tubular members configured to contain, deliver or deploy a closure element, the tube set having a distal end and a proximal end, the proximal end of the tube set being coupled to the handle member, wherein the closure element is disposed within the tube set in an open configuration;
an inner lumen disposed at least partially within the tube set;
a plunger member movably coupled to the handle member; and
an anchor member at least partially disposed within the inner lumen, the anchor member comprising a first elongated portion, a second elongated portion, and an anchor portion with at least two looped portions, the first elongated portion, the second elongated portion, and the anchor member, with the at least two looped portions, being continuously connected from the first elongated portion to the second elongated portion, the anchor portion being disposed in the inner lumen in an initial configuration and configured to move to an expanded configuration once deployed from within the inner lumen without additional external force, wherein distal movement of the plunger member deploys the anchor member to the expanded configuration and proximal movement of the plunger member retracts the anchor member back to the initial configuration, the expanded configuration including a first portion and a second portion, the second portion being an inverted mirror image of the first portion about an intersection between the first portion and the second portion the anchor member configured to locate the closure system within a body lumen, the anchor member being configured to be retracted through the closure element.

19. The closure system of claim 18, the inner lumen being movable relative to the tube set and handle member and the anchor member comprising shape memory or superelastic materials.

20. The closure system of claim 18, the anchor portion further comprising an elongate wire forming the first and second elongate portions and the anchor portion.

21. The closure system of claim 18, wherein the first and second elongate portions of the anchor member are coupled to the plunger member.

22. The closure system of claim 18, wherein the one or more tubular members comprise a garage tube, a pusher tube, and a carrier tube.

23. A method of closing a body lumen opening having a lumen wall comprising:
advancing a closure system at least partially into a body lumen opening, the closure system comprising:
a handle member;
a tube set configured to deliver or deploy a closure element, the tube set having a distal end and a proximal end, the proximal end of the tube set being coupled to the handle member;
an inner lumen disposed at least partially within the tube set;
a plunger member movably coupled to the handle member; and
an anchor member at least partially disposed within the inner lumen, the anchor member comprising an anchor portion having at least two looped portions and a pair of elongate portions, the anchor portion, with the at least two looped portions, and the pair of elongate portions being continuously connected together, the anchor portion being disposed in the inner lumen in an initial configuration and configured to move to an expanded configuration in a transverse plane to said first elongate portion and said second elongate portion once deployed from the inner lumen without external force, the expanded configuration including a first portion and a second portion, the second portion being an inverted mirror image of the first portion about an intersection between the first portion and the second portion, the first elongate portion, the second elongate portion, the first portion, and the inverted second portion are continuously connected the anchor member configured to locate the closure system within the body lumen, the anchor member being configured to be retracted through the closure element;
deploying the anchor portion of the anchor member within the body lumen;
positioning the anchor portion of the anchor member against a distal surface of the lumen wall proximate the body lumen opening;
advancing the tube set in a distal direction to position the distal end of the tube set against a proximal surface of the lumen wall proximate the body lumen opening; and
deploying a closure element into the lumen wall proximate the body lumen opening to close the body lumen opening.

24. The method of claim 23, further comprising advancing the plunger member to deploy the anchor portion of the anchor member and retracting the plunger member to retract the anchor portion of the anchor member.

* * * * *